US008431591B2

(12) United States Patent
Neumeyer et al.

(10) Patent No.: US 8,431,591 B2
(45) Date of Patent: Apr. 30, 2013

(54) R(−)-2-METHOXY-11-HYDROXYAPORPHINE AND DERIVATIVES THEREOF

(75) Inventors: John L. Neumeyer, Wayland, MA (US); Yu-Gui Si, Waltham, MA (US)

(73) Assignee: The McLean Hospital Corporation, Belmont, MA (US)

( * ) Notice: Subject to any disclaimer, the term of this patent is extended or adjusted under 35 U.S.C. 154(b) by 274 days.

(21) Appl. No.: 12/668,617

(22) PCT Filed: Jul. 10, 2008

(86) PCT No.: PCT/US2008/008449
§ 371 (c)(1),
(2), (4) Date: Oct. 22, 2010

(87) PCT Pub. No.: WO2009/009083
PCT Pub. Date: Jan. 15, 2009

(65) Prior Publication Data
US 2011/0034446 A1 Feb. 10, 2011

Related U.S. Application Data

(60) Provisional application No. 60/959,324, filed on Jul. 12, 2007.

(51) Int. Cl.
*A61K 31/473* (2006.01)
*C07D 221/18* (2006.01)
(52) U.S. Cl.
USPC ............................................ 514/284; 546/75
(58) Field of Classification Search .................. 514/284; 546/75
See application file for complete search history.

(56) References Cited

U.S. PATENT DOCUMENTS

| 4,687,773 | A | 8/1987 | Neumeyer et al. |
| 5,258,384 | A | 11/1993 | Cannon et al. |
| 5,744,476 | A | 4/1998 | Locke et al. |
| 5,994,363 | A | 11/1999 | El-Rashidy et al. |
| 6,313,134 | B1 | 11/2001 | Su et al. |
| 7,057,044 | B2 | 6/2006 | Su et al. |
| 7,648,995 | B2 | 1/2010 | Neumeyer et al. |
| 8,063,060 | B2 | 11/2011 | Neumeyer et al. |
| 2010/0081651 | A1 | 4/2010 | Neumeyer et al. |

FOREIGN PATENT DOCUMENTS

| WO | WO 90/12574 | 11/1990 |
| WO | WO 02/14279 | 2/2002 |
| WO | WO 2005/099702 | 10/2005 |
| WO | WO-2011/130530 A1 | 10/2011 |

OTHER PUBLICATIONS

Atkinson et al. "Derivatives of Apomorphine and of Other N-Substituted Norapomorphines," *J. Pharmacol. Sci.* 65:1682-1685 (1976).
Baldessarini et al. "Esters of Apomorphine and N,N-Dimethyldopamine as Agonists of Dopamine Receptors in the Rat Brain In Vivo," *Neuropharmacology* 14:725-731 (1975).
Baldessarini et al., "Prolonged Apomorphine-Like Behavioural Effects of Apomorphine Esters," *Neuropharmacology* 15:471-478 (1976).
Baldessarini et al., "Prolonged D2 Antidopaminergic Activity of Alkylating and Nonalkylating Derivatives of Spiperone in Rat Brain," *Mol. Pharmacol.* 42:856-863 (1992).
Baldessarini et al., "Receptor Affinities of Aporphine Enantiomers in Rat Brain Tissue," *Eur. J. Pharmacol.* 254:199-203 (1994).
Bentley and Cardwell, "The Morphine—the Baine Group of Alkaloids," *J. Chem. Soc.* 3252-3260 (1955).
Berenyi et al., "Preparation of Demethoxyoripavine and Its Conversion into N-Substituted N-Demethylapomorphine Derivatives," Acta Chim. Hung. 113:51-60 (1983).
Berenyi et al., "Synthesis of New N-Substituted N-Demethylaporphine Derivatives," *Acta Chim. Hung.* 120:201-205 (1985).
Berenyi et al., "A New Efficient Method for the Preparation of 2-Fluoro-N-propylnorapomorphine," *J. Chem. Soc. Perkin Trans.* I.:2693-2694 (1992).
Berenyi et al., "Rearrangement of Morphinandienes in Methanesulfonic Acid," *J. Chem. Perkin Trans.* I:2137-2139 (1993).
Borgman et al. "Diester Derivatives as Apomorphine Prodrugs," *J. Med. Chem.* 19:717-719 (1976).
Campbell et al., "Behavioral Effects of (−)10,11-Methylenedioxy-N-n-propylnoraporphine, An Orally Effective Long-Acting Agent Active at Central Dopamine Receptors, and Analogous Aporphines," *Neuropharmacology* 21:953-961 (1982).
Campbell et al., "R(−) and S(+) Stereoisomers of 11-Hydroxy- and 11-Methoxy-N-n-Propylnoraporphine: Central Dopaminergic Behavioral Activity in the Rat." *Neuropharmacology*. 29(6):527-536. (1990).
Campbell et al., "Selective Antidopaminergic Effects of S(+)N-n-propylnoraporphines in Limbic Versus Extrapyramidal Sites in Rat Brain: Comparisons with Typical and Atypical Antipsychotic Agents" *Psychopharmacology* (Berl.) 103:323-329 (1991).
Cannon et al., "(R)-(−)-10-Methyl-11-hydroxyaporphine: a Highly Selective Serotonergic Agonist," *J. Med. Chem.* 31:313-318 (1988).
Csutoras et al. "Synthesis and Neuropharmacological Evaluation of R(−)-N-alkyl-11-hydroxynoraporphines and Their Esters," *Bioinorg. Med. Chem.* 12:3553-3559 (2004).
Gao et al. "Synthesis and Dopamine Agonist and Antagonist Effects of (R)-(−)-and (S)-(+)-11-Hydroxy-N-n-propylnoraporphine," *J. Med. Chem.* 31:1392-1396 (1988).
Granchelli et al., "Aporphines. 27. Mechanistic Aspects of the Rearrangement of Thebaine and Codeine Analogues in Methanesulfonic Acid. Improved Method for Synthesis of N-Alkylated Aporphines," *J. Org. Chem.* 45:2275-2282 (1980).
Hedberg et al., "(R)-11-Hydroxy- and (R)-11-Hydroxy-10-methylaporphine: Synthesis, Pharmacology, and Modeling of $D_{2A}$ and $5-HT_{1A}$ Receptor Interactions,"*J. Med. Chem.* 38:647-658 (1995).
Joyce, "Multiple Dopamine Receptors and Behavior," *Neurosci. Biobehav. Rev.* 7:227-256 (1983).
Kula et al., "RBI-257: A Highly Potent Dopamine $D_4$ Receptor-Selective Ligand," *Eur. J. Pharmacol* 331:333-336 (1997).

(Continued)

*Primary Examiner* — Charanjit Aulakh
(74) *Attorney, Agent, or Firm* — Clark & Elbing LLP

(57) ABSTRACT

The invention features derivatives of R(−)-2-methoxy-11-hydroxyaporphines and methods of treating Parkinson's disease and sexual dysfunction therewith.

19 Claims, No Drawings

OTHER PUBLICATIONS

Kula et al., "[3H]β-CIT: A Radioligand for Dopamine Transporters in Rat Brain Tissue," *Eur. J. Pharmacol.* 385:291-294 (1999).

Makleit et al., "Conversions of Tosyl and Mesyl Derivatives of the morphine Group, XI," *Acta Chim. Sci. Hung.* 74:111-113 (1972).

Martinez et al. "Clinical Experience with Apomorphine Hydrochloride: the First 107 Patients," *J. Urology* 170:2352-2355 (2003).

Neumeyer and Granchelli, "Aporphines. 11. Synthesis and Dopaminergic Activity of Monohydroxyaporphines. Total synthesis of (+,–)-11-Hydroxyaporphine, (+,–)-11-Hydroxynoraporphine, and (+,–)-11-Hydroxy-N-n-propylnoraporphine," *J. Med. Chem.* 17:1090-1095 (1974).

Neumeyer et al. "Aporphines, 36. Dopamine Receptor Interactions of Trihydroxyaporphines. Synthesis, Radioreceptor Binding, and Striatal Adenylate Cyclase Stimulation of 2,10,11-Trihydroxyaporphines in Comparison with Other Hydroxylated Aporphines," *J. Med. Chem* 24:1440-1445 (1981).

Neumeyer et al., "Aporphines 65: Chemical, Microbial Synthesis and Characterization by Gas Chromatography/Mass Spectrometry of (R)-(–)-10-Hydroxy 11-Methoxy-N-n-Propylnoraporphine, a Potential Metabolite of N-n-Propylnorapomorphine." *Biomed. Environ. Mass Spectrom.* 13(5):223-229 (1986).

Neumeyer et al., "R and S Enantiomers of 11-Hydroxy- and 10,11-Dihydroxy-N-allylnoraporphine: Synthesis and Affinity for Dopamine Receptors in Rat Brain Tissue," *J. Med. Chem.* 34:24-28 (1991).

Neumeyer and Baldessarini, "Apomorphine: New Uses for an Old Drug," *Pharmaceut. News* 4:12-16 (1997).

Neumeyer et al., "Therapeutic and Diagnostic Agents for Parkinson's Disease" Chapter 12, vol. 6, Abraham D (ed): Burger's Medicinal Chemistry and Drug Discovery, 6th Edition. New York, John Wiley & Sons, pp. 711-741 (2003).

Ram and Neumeyer, "Aporphines. 42. Synthesis of (R)-(–)-11-Hydroxyaporphines from Morphine," *J. Org. Chem.* 47:4372-4374 (1982).

Ram and Neumeyer, "Synthesis of (R)-1,2,11-Trihydroxy-, (R)-2,11-, and (R)-2,10-Dihydroxyaporphines—Non Naturally Occurring Aporphine Alkaloids from Pukateine and Thebaine," *J. Heterocyclic Chem.* 28:1721-1724 (1991).

Rodenhuis, et al. "Dopamine $D_2$ activity of R-(–)-Apomorphine and Selected Analogs: a Microdialysis Study," *Eur. J. Pharmacol.* 387:39-45 (2000).

Scatton and Worms, "Subsensitivity of Striatal and Mesolimbic Dopamine Target Cells after Repeated Treatment with Apomorphine Dipivaloyl Ester," *Naunym-Schmiedeberg's Arch. Pharmacol.* 303:271-278 (1978).

Scatton and Worms, "Tolerance to Increases in Striatal Acetylcholine Concentrations after Repeated Administration of Apomorphine Dipivaloyl Ester," *J. Pharm. Pharmacol.* 31:861-863 (1979).

Schaus et al., "Aporphines as Antagonists of Dopamine D-1 Receptors," *J. Med. Chem.* 33:600-607 (1990).

Simon et al. "Synthesis of C-3 Halogene-Substituted Apocodeins and Apomorphines," *Synth Commun.* 21:2309-2316 (1991).

Sit, "Dopamine Agonists in the Treatment of Parkinson's Disease—Past, Present and Future," *Current Pharmaceutical Design* 6:1211-1248 (2000).

Ungerstedt, "Striatal Dopamine Release after Amphetamine or Nerve Degeneration Revealed by Rotational Behaviour," *Acta Physiol. Scand. Suppl.* 367:49-68 (1971).

Weiss and Daum, "Derivatives of Morphine. IV.[1] 14-Hydroxymorphine and 14-Hydroxydihydromorphine," *J. Med. Chem.* 39:123-125 (1965).

Worms and Scatton, "Tolerance to Stereotyped Behavior and to Decrease in Striatal Homovanillic Acid Levels after Repeated Treatment with Apomorphine Dipivaloyl Ester," *Eur. J. Pharmacol.* 45:395-396 (1977).

Yu, "Thaliporphine Selectively Inhibits Expression of the Inducible, but not the Constitutive, Nitric Oxide Synthase," *Biochem. J.* 303:289-294 (1994).

Zhang et al., "Nigrostriatal Dopaminergic Denervation Enhances Dopamine $D_4$ Receptor Binding in Rat Caudate-Putamen," *Pharmacol. Biochem. Behav.* 39:111-116 (2001).

Zhang et al., "Role of Dopamine D4 receptors in motor Hyperactivity Induced by Neonatal 6-hydroxydopamine lesions in rats," *Neuropsychopharmacology* 25:624-632 (2001).

Zijlstra et al. "Behavior of Reaction Mixtures under Microwave Conditions: Use of Sodium Salts in Microwave-Induced N-[$^{18}$F]Fluoroalkylations of Aporphine and Tetralin Derivatives," *J. Org. Chem.* 58:1643-1645 (1993).

International Search Report from International Application No. PCT/US2008/008449, dated Oct. 7, 2008 (date of mailing of report).

International Preliminary Report on Patentability from International Application No. PCT/US2008/008449, dated Jan. 12, 2010 (date of issuance of report).

Granchelli et al., "Aporphines. 23. Normorphothebaine Derivatives: Synthesis of an Aporphine Nitrogen Mustard," *J. Org. Chem.* 42:2014-2017, 1977.

Si et al., "Synthesis and dopamine receptor affinities of N-alkyl-11-hydroxy-2-methoxynoraporphines: N-alkyl Substituents Determine D1 Versus D2 Receptor Selectivity," *J. Med. Chem.* 51:983-987, 2008.

R(−)-2-METHOXY-11-HYDROXYAPORPHINE AND DERIVATIVES THEREOF

CROSS REFERENCE TO RELATED APPLICATIONS

This application is the U.S. National Stage of International Application PCT/US2008/008449, filed Jul. 10, 2008, which claims the benefit of U.S. Provisional Application Ser. No. 60/959,324, which was filed on Jul. 12, 2007, each of which is incorporated herein by reference.

BACKGROUND OF THE INVENTION

The invention relates to the treatment of Parkinson's disease, sexual dysfunction, and depressive disorders.

Parkinson's disease is a progressive neurodegenerative disorder of the basal ganglia of the brain, which most often becomes apparent after the age of 55. It is a prevalent and prototypic hypokinetic disorder, with akinesia, bradykinesia, rigidity and tremor as the most prominent features. The neurological and psychiatric symptoms, including depression and psychosis, with late dementia, usually worsen with time. The neuropathology of Parkinson's disease reveals a striking and selective loss of the dopaminergic neurons of the nigrostriatal pathway of the brain.

As Parkinson's disease is associated with a loss of the neurotransmitter dopamine, it is commonly treated with drugs which replace or mimic the actions of dopamine. Since dopamine itself cannot pass the blood-brain diffusion barrier, the most commonly used therapy is levodopa (L-DOPA), the immediate precursor of dopamine which is readily decarboxylated by remaining dopaminergic neurons and other amine-producing neurons. A complication of long-term treatment with L-DOPA is the development of rapid fluctuations in clinical state such that the patient changes, often abruptly, between mobility and immobility; this phenomenon is known as the 'on-off' effect.

An alternative approach to treatment with L-DOPA is the use of drugs (dopamine agonists and partial-agonists) that mimic the actions of dopamine. Treatment with dopamine receptor agonists has some advantages over treatment with L-DOPA. Unlike L-DOPA, dopamine agonists are effective in patients with advanced stages of Parkinson's disease because their action at postsynaptic receptors is unaffected by the lack of dopamine producing nerve cells that decarboxylate L-DOPA to produce dopamine locally, whereas the denervated dopamine receptors are supersensitive to agonists. Furthermore, there is an increasing interest in the potential of dopamine receptor agonists to provide a neuroprotective effect. Theoretically, such a protective effect might result from (i) a decreased need for the use of L-DOPA, a substance that may cause oxidative stress and perhaps even contribute to further damage of dopamine neurons, (ii) stimulation of dopamine autoreceptors resulting in decreased dopamine synthesis, release, and turnover, resulting in reduced metabolism of dopamine to reactive oxygen species, and (iii) by direct anti-oxidant effects.

R(−)-Apomorphine is a directly acting dopamine agonist at both $D_1$ and $D_2$ receptors, and dopamine autoreceptors, without opiate-like or addictive properties. Apomorphine therapy has led to sustained improvements in Parkinson's disease patients with refractory motor oscillations (on-off phenomena). However, it is difficult to administer owing to its poor bioavailability and extensive first-pass metabolism to inactive metabolites. Therefore, apomorphine is usually administered either by intermittent subcutaneous injection or continuous subcutaneous infusion. Following a single dose, apomorphine has an onset of action of 5-15 minutes, and its effects last for 40-60 minutes.

Direct dopamine agonists, including R(−)-apomorphine, are also effective in the treatment of a number of forms of sexual dysfunction, primarily, but not limited to erectile dysfunction. See Martinez et al., *J. Urology* 170:2352 (2003).

New compounds that overcome the practical problems associated with apomorphine therapy, particularly its lack of oral bioavailability and short half-life, are needed for the treatment of diseases, such as Parkinson's disease and erectile dysfunction.

SUMMARY OF THE INVENTION

The invention is based on the discovery of R(−)-2-methoxy-11-hydroxyaporphine derivatives and synthetic methods for producing the derivatives. The compounds are useful for the treatment of diseases, such as Parkinson's disease, sexual dysfunction, and depressive disorders.

In a first aspect, the invention features a compound of formula I or a pharmaceutically acceptable salt or solvate thereof.

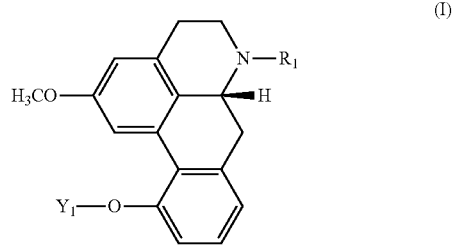

(I)

In formula I, $Y_1$ is H, C(O)—$R_3$, C(O)—O—$R_3$, C(O)—$NR_3R_4$, P(O)(OH)—O—$R_3$, C(S)—$R_3$, C(S)—O—$R_3$, C(S)—$NR_3R_4$, or fatty acid acyl; $R_1$ is H, $C_{1-4}$ alkyl, $C_{2-4}$ alkenyl, or $C_{2-4}$ alkynyl; and each of $R_3$ and $R_4$ is, independently, selected from H, $C_{1-12}$ alkyl, $C_{2-12}$ alkenyl, $C_{2-12}$ alkynyl, $C_{2-6}$ heterocyclyl, $C_{6-12}$ aryl, $C_{7-14}$ alkaryl, $C_{3-10}$ alkheterocyclyl, and $C_{1-7}$ heteroalkyl, or $R_3$ and $R_4$ together form a heterocyclic ring containing at least one nitrogen atom. Desirably, $R_1$ is H, $CH_3$, $CH_2CH_3$, $CH_2CH_2CH_3$, $CH_2CH_2$=$CH_2$, $CH_2C$≡$CH$, $CH_2CH_2CH_2CH_3$, or cyclopropylmethyl.

Compounds of formula I include R(−)-2-methoxy-11-hydroxy-N-n-propyl-noraporphine, R(−)-2-methoxy-11-hydroxy-N-methyl-noraporphine, R(−)-2-methoxy-11-hydroxy-N-ethyl-noraporphine, R(−)-2-methoxy-11-hydroxy-N-cyclopropylmethyl-noraporphine, R(−)-2-methoxy-11-hydroxy-N-allyl-noraporphine, R(−)-2-methoxy-11-hydroxy-N-propargyl-noraporphine, R(−)-2-methoxy-11-hydroxy-N-butyl-noraporphine, R(−)-2-methoxy-11-O-acetyl-N-n-propyl-noraporphine, R(−)-2-methoxy-11-O-propionyl-N-n-propyl-noraporphine, R(−)-2-methoxy-11-O-isobutyryl-N-n-propyl-noraporphine, R(−)-2-methoxy-11-O-butyryl-N-n-propyl-noraporphine, R(−)-2-methoxy-11-O-isovaleryl-N-n-propyl-noraporphine, R(−)-2-methoxy-11-O-valeryl-N-n-propyl-noraporphine, R(−)-2-methoxy-11-O-methylcarbamoyl-N-n-propyl-noraporphine, R(−)-2-methoxy-11-O-ethylcarbamoyl-N-n-propylnoraporphine, R(−)-2-methoxy-11-O-isopropylcarbamoyl-N-n-propylnoraporphine, R(−)-2-methoxy-11-O-n-propylcarbamoyl-N-n-propylnoraporphine, R(−)-2-methoxy-11-O-isobutylcarbamoyl-N-n-propylnoraporphine, and R(−)-2-methoxy-11-O-n-butylcarbamoyl-N-n-propylnoraporphine.

The invention also features a pharmaceutical composition comprising a compound of the invention together with a pharmaceutically acceptable excipient.

The invention features a method for treating Parkinson's disease, sexual dysfunction, or depressive disorders in a patient, e.g., a human patient, by administering an effective amount of a compound of the invention. These compounds are particularly useful for treating depressive disorders, such as major depression, dysthymia, bipolar disorder (manic depression), and post traumatic stress disorder.

The compounds of the invention can be administered systemically, including, for example, by intravenous, intramuscular, or subcutaneous injection, orally, by inhalation, or by topical or transdermal application. Alternatively, the compounds can be centrally administered using, for example, by an intrathecal, intracerebroventricular, or intraparenchemal injection. Desirably, the compounds are administered orally.

For any of the above methods, the method optionally includes the step of administering an effective amount of an anti-emetic agent to the patient simultaneously, or within one day, of administering the compound of the invention. An effective amount is an amount that reduces or prevents emesis and/or nausea in the patient. Anti-emetic agents which can be used in the methods of the invention include, without limitation, nicotine, lobeline sulfate, pipamazine, oxypendyl hydrochloride, ondansetron, buclizine hydrochloride, cyclizine hydrochloride, dimenhydrinate, scopolamine, metopimazine, diphenhydramine, and diphenidol hydrochloride.

The invention further features a method for synthesizing a compound of formula III from a compound of formula II by reducing the compound of formula II with magnesium metal in methanol in the presence of Pd/C catalyst.

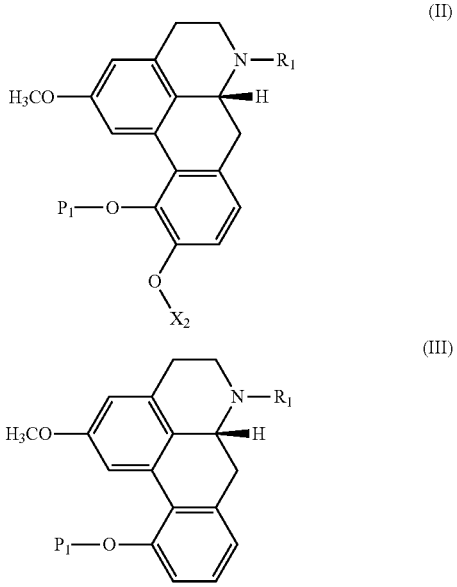

In formulas II and III, $P_1$ is H, or a hydroxyl protecting group other than $CH_3SO_2$— or $CF_3SO_2$—; $X_2$ is $CH_3SO_2$— or $CF_3SO_2$—; and $R_1$ is H, $C_{1-4}$ alkyl, $C_{2-4}$ alkenyl, $C_{2-4}$ alkynyl, or an amine protecting group. In certain embodiments, $P_1$ is H, C(O)—$R_3$, C(O)—O—$R_3$, C(O)—$NR_3R_4$, or $SiR_3R_4R_5$; and each of $R_3$, $R_4$, and $R_5$ is, independently, selected from H, $C_{1-12}$ alkyl, $C_{2-12}$ alkenyl, $C_{2-12}$ alkynyl, $C_{2-6}$ heterocyclyl, $C_{6-12}$ aryl, $C_{7-14}$ alkaryl, $C_{3-10}$ alkheterocyclyl, and $C_{1-7}$ heteroalkyl, or $R_3$ and $R_4$ together form a heterocyclic ring containing at least one nitrogen atom. In still other embodiments, the reduction is carried out in a solution including ammonium acetate. Desirably, the compound of formula III is used in the preparation of a compound of the invention (e.g., the hydroxyl group at position 11 is modified as described herein to produce, for example, an ester or carbamate derivative of R(−)-2-methoxy-11-hydroxyaporphine).

The term "administration" or "administering" refers to a method of giving a dosage of a pharmaceutical composition to a patient, where the method is, e.g., oral, topical, transdermal, by inhalation, intravenous, intraperitoneal, intracerebroventricular, intrathecal, or intramuscular. The preferred method of administration can vary depending on various factors, e.g., the components of the pharmaceutical composition, site of administration, and severity of the symptoms being treated.

As used herein, the term "treating" refers to administering a pharmaceutical composition for prophylactic and/or therapeutic purposes. To "prevent disease" refers to prophylactic treatment of a patient who is not yet ill, but who is susceptible to, or otherwise at risk of, a particular disease. To "treat disease" or use for "therapeutic treatment" refers to administering treatment to a patient already suffering from a disease to ameliorate the disease and improve the patient's condition. Thus, in the claims and embodiments, treating is the administration to a patient either for therapeutic or prophylactic purposes.

As used herein, "sexual dysfunction" refers to disorders of orgasm, response timing, ejaculation, nociception, congestive arousal and erection, vasculogenic impairment, or desire. In males, the form of sexual dysfunction is typically erectile dysfunction, the inability to achieve and sustain an erection sufficient for intercourse. Females also can have sexual dysfunctions of arousal and orgasm that increase with age and are associated with the presence of vascular risk factors and onset of menopause. Some of the vascular and muscular mechanisms that contribute to penile erection in the male are believed to involve similar vasculogenic factors in female genital responses. Female sexual dysfunction includes a failure to attain or maintain vaginal lubrication-swelling responses of sexual excitement until completion of the sexual activity.

By "depressive disorder" is meant any psychological or psychiatric disorder associated with symptoms of depressed mood. Treatable depressive disorders may be characterized by an inhibition or reduction of dopaminergic function in the nucleus accumbens, e.g., major depression, dysthymia, bipolar disorder (manic depression), and post-traumatic stress disorder.

The compounds and formulas described herein include addition salts, solvates, and polymorphs, thereof.

In the generic descriptions of compounds of this invention, the number of atoms of a particular type in a substituent group is generally given as a range, e.g., an alkyl group containing from 1 to 4 carbon atoms or $C_{1-4}$ alkyl. Reference to such a range is intended to include specific references to groups having each of the integer number of atoms within the specified range. For example, an alkyl group from 1 to 4 carbon atoms includes each of $C_1$, $C_2$, $C_3$, and $C_4$. A $C_{1-12}$ heteroalkyl, for example, includes from 1 to 12 carbon atoms in addition to one or more heteroatoms. Other numbers of atoms and other types of atoms may be indicated in a similar manner.

As used herein, the terms "alkyl" and the prefix "alk-" are inclusive of both straight chain and branched chain groups and of cyclic groups, i.e., cycloalkyl. Cyclic groups can be monocyclic or polycyclic and preferably have from 3 to 6 ring carbon atoms, inclusive. Exemplary cyclic groups include cyclopropyl, cyclobutyl, cyclopentyl, and cyclohexyl groups.

By "$C_{1-4}$ alkyl" is meant a branched or unbranched hydrocarbon group having from 1 to 4 carbon atoms. A $C_{1-4}$ alkyl group may be substituted or unsubstituted. Exemplary substituents include alkoxy, aryloxy, sulfhydryl, alkylthio, arylthio, halide, hydroxyl, fluoroalkyl, perfluoralkyl, amino, aminoalkyl, disubstituted amino, quaternary amino, hydroxyalkyl, carboxyalkyl, and carboxyl groups. $C_{1-4}$ alkyls include, without limitation, methyl, ethyl, n-propyl, isopropyl, cyclopropyl, cyclopropylmethyl, n-butyl, iso-butyl, sec-butyl, tert-butyl, and cyclobutyl.

By "$C_{1-12}$ alkyl" is meant a branched or unbranched hydrocarbon group having from 1 to 12 carbon atoms. A $C_{1-12}$ alkyl may be substituted or unsubstituted, may optionally include monocyclic or polycyclic rings, and includes the $C_{1-4}$ alkyls above.

By "$C_{2-4}$ alkenyl" is meant a branched or unbranched hydrocarbon group containing one or more double bonds and having from 2 to 4 carbon atoms. A $C_{2-4}$ alkenyl may optionally include monocyclic or polycyclic rings, in which each ring desirably has from three to six members. The $C_{2-4}$ alkenyl group may be substituted or unsubstituted. Exemplary substituents include alkoxy, aryloxy, sulfhydryl, alkylthio, arylthio, halide, hydroxyl, fluoroalkyl, perfluoralkyl, amino, aminoalkyl, disubstituted amino, quaternary amino, hydroxyalkyl, carboxyalkyl, and carboxyl groups. $C_{2-4}$ alkenyls include, without limitation, vinyl, allyl, 2-cyclopropyl-1-ethenyl, 1-propenyl, 1-butenyl, 2-butenyl, 3-butenyl, 2-methyl-1-propenyl, and 2-methyl-2-propenyl.

By "$C_{2-12}$ alkenyl" is meant a branched or unbranched hydrocarbon group containing one or more double bonds and having from 2 to 12 carbon atoms. A $C_{2-12}$ alkenyl may be substituted or unsubstituted, may optionally include monocyclic or polycyclic rings, and includes the $C_{2-4}$ alkenyls above.

By "$C_{2-4}$ alkynyl" is meant a branched or unbranched hydrocarbon group containing one or more triple bonds and having from 2 to 4 carbon atoms. The $C_{2-4}$ alkynyl group may be substituted or unsubstituted. Exemplary substituents include alkoxy, aryloxy, sulfhydryl, alkylthio, arylthio, halide, hydroxy, fluoroalkyl, perfluoralkyl, amino, aminoalkyl, disubstituted amino, quaternary amino, hydroxyalkyl, carboxyalkyl, and carboxyl groups. $C_{2-4}$ alkynyls include, without limitation, ethynyl, 1-propynyl, 2-propynyl, 1-butynyl, 2-butynyl, and 3-butynyl.

By "$C_{2-12}$ alkynyl" is meant a branched or unbranched hydrocarbon group containing one or more triple bonds and having from 2 to 12 carbon atoms. A $C_{2-12}$ alkynyl may be substituted or unsubstituted, may optionally include monocyclic or polycyclic rings, and includes $C_{2-4}$ alkynyls above.

By "$C_{2-6}$ heterocyclyl" is meant a stable 5- to 7-membered monocyclic or 7- to 14-membered bicyclic heterocyclic ring which is saturated partially unsaturated or unsaturated (aromatic), and which consists of 2 to 6 carbon atoms and 1, 2, 3 or 4 heteroatoms independently selected from N, O, and S and including any bicyclic group in which any of the above-defined heterocyclic rings is fused to a benzene ring. The heterocyclyl group may be substituted or unsubstituted. Exemplary substituents include alkoxy, aryloxy, sulfhydryl, alkylthio, arylthio, halide, hydroxy, fluoroalkyl, perfluoralkyl, amino, aminoalkyl, disubstituted amino, quaternary amino, hydroxyalkyl, carboxyalkyl, and carboxyl groups. The nitrogen and sulfur heteroatoms may optionally be oxidized. The heterocyclic ring may be covalently attached via any heteroatom or carbon atom which results in a stable structure, e.g., an imidazolinyl ring may be linked at either of the ring-carbon atom positions or at the nitrogen atom. A nitrogen atom in the heterocycle may optionally be quaternized. Preferably when the total number of S and O atoms in the heterocycle exceeds 1, then these heteroatoms are not adjacent to one another. Heterocycles include, without limitation, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5, 2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl. Preferred 5 to 10 membered heterocycles include, but are not limited to, pyridinyl, pyrimidinyl, triazinyl, furanyl, thienyl, thiazolyl, pyrrolyl, pyrazolyl, imidazolyl, oxazolyl, isoxazolyl, tetrazolyl, benzofuranyl, benzothiofuranyl, indolyl, benzimidazolyl, 1H-indazolyl, oxazolidinyl, isoxazolidinyl, benzotriazolyl, benzisoxazolyl, oxindolyl, benzoxazolinyl, quinolinyl, and isoquinolinyl. Preferred 5 to 6 membered heterocycles include, without limitation, pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl.

By "$C_{6-12}$ aryl" is meant an aromatic group having a ring system comprised of carbon atoms with conjugated π electrons (e.g., phenyl). The aryl group has from 6 to 12 carbon atoms. Aryl groups may optionally include monocyclic, bicyclic, or tricyclic rings, in which each ring desirably has five or six members. The aryl group may be substituted or unsubstituted. Exemplary substituents include alkyl, hydroxy, alkoxy, aryloxy, sulfhydryl, alkylthio, arylthio, halide, fluoroalkyl, carboxyl, hydroxyalkyl, carboxyalkyl, amino, aminoalkyl, monosubstituted amino, disubstituted amino, and quaternary amino groups.

By "$C_{7-14}$ alkaryl" is meant an alkyl substituted by an aryl group (e.g., benzyl, phenethyl, or 3,4-dichlorophenethyl) having from 7 to 14 carbon atoms.

By "$C_{3-10}$ alkheterocyclyl" is meant an alkyl substituted heterocyclic group having from 3 to 10 carbon atoms in addition to one or more heteroatoms (e.g., 3-furanylmethyl, 2-furanylmethyl, 3-tetrahydrofuranylmethyl, or 2-tetrahydrofuranylmethyl).

By "$C_{1-7}$ heteroalkyl" is meant a branched or unbranched alkyl, alkenyl, or alkynyl group having from 1 to 7 carbon atoms in addition to 1, 2, 3 or 4 heteroatoms independently selected from the group consisting of N, O, S, and P. Heteroalkyls include, without limitation, tertiary amines, secondary amines, ethers, thioethers, amides, thioamides, carbamates, thiocarbamates, hydrazones, imines, phosphodiesters, phosphoramidates, sulfonamides, and disulfides. A heteroalkyl may optionally include monocyclic, bicyclic, or tricyclic rings, in which each ring desirably has three to six members. The heteroalkyl group may be substituted or unsubstituted. Exemplary substituents include alkoxy, aryloxy, sulfhydryl, alkylthio, arylthio, halide, hydroxyl, fluoroalkyl, perfluoroalkyl, amino, aminoalkyl, disubstituted amino, quaternary amino, hydroxyalkyl, hydroxyalkyl, carboxyalkyl, and carboxyl groups. Examples of $C_{1-7}$ heteroalkyls include, without limitation, methoxymethyl and ethoxyethyl.

By "halide" is meant bromine, chlorine, iodine, or fluorine.

By "fluoroalkyl" is meant an alkyl group that is substituted with a fluorine atom.

By "perfluoroalkyl" is meant an alkyl group consisting of only carbon and fluorine atoms.

By "carboxyalkyl" is meant a chemical moiety with the formula —(R)—COOH, wherein R is selected from $C_{1-7}$ alkyl, $C_{2-7}$ alkenyl, $C_{2-7}$ alkynyl, $C_{2-6}$ heterocyclyl, $C_{6-12}$ aryl, $C_{7-14}$ alkaryl, $C_{3-10}$ alkheterocyclyl, or $C_{1-7}$ heteroalkyl.

By "hydroxyalkyl" is meant a chemical moiety with the formula —(R)—OH, wherein R is selected from $C_{1-7}$ alkyl, $C_{2-7}$ alkenyl, $C_{2-7}$ alkynyl, $C_{2-6}$ heterocyclyl, $C_{6-12}$ aryl, $C_{7-14}$ alkaryl, $C_{3-10}$ alkheterocyclyl, or $C_{1-7}$ heteroalkyl.

By "alkoxy" is meant a chemical substituent of the formula —OR, wherein R is selected from $C_{1-7}$ alkyl, $C_{2-7}$ alkenyl, $C_{2-7}$ alkynyl, $C_{2-6}$ heterocyclyl, $C_{6-12}$ aryl, $C_{7-14}$ alkaryl, $C_{3-10}$ alkheterocyclyl, or $C_{1-7}$ heteroalkyl.

By "aryloxy" is meant a chemical substituent of the formula —OR, wherein R is a $C_{6-12}$ aryl group.

By "alkylthio" is meant a chemical substituent of the formula —SR, wherein R is selected from $C_{1-7}$ alkyl, $C_{2-7}$ alkenyl, $C_{2-7}$ alkynyl, $C_{2-6}$ heterocyclyl, $C_{6-12}$ aryl, $C_{7-14}$ alkaryl, $C_{3-10}$ alkheterocyclyl, or $C_{1-7}$ heteroalkyl.

By "arylthio" is meant a chemical substituent of the formula —SR, wherein R is a $C_{6-12}$ aryl group.

By "quaternary amino" is meant a chemical substituent of the formula —(R)—N(R')(R'')(R''')$^+$, wherein R, R', R'', and R''' are each independently an alkyl, alkenyl, alkynyl, or aryl group. R may be an alkyl group linking the quaternary amino nitrogen atom, as a substituent, to another moiety. The nitrogen atom, N, is covalently attached to four carbon atoms of alkyl and/or aryl groups, resulting in a positive charge at the nitrogen atom.

By "fatty acid acyl" is meant a chemical moiety with the formula R—C(O)—, wherein R is a partially-saturated straight chain or branched hydrocarbon group having between 12 and 26 carbon atoms. Fatty acid acyls are derived from fatty acids including, without limitation, those occurring naturally in the brain. For example, fatty acids having 16 carbon atoms and 0, 1 or 2 double bonds (C16:0; C16:1 and C16:2), those with 18 carbon atoms and 1, 2 or 3 double bonds (C18:1; C18:2; and C18:3), those with 20 carbon atoms and 1, 2 or 4 double bonds (C20:1; C20:2; and C20:4) and those with 22 carbon atoms and 4, 5 or 6 double bonds (C22:4; C22:5 and C22:6). The fatty acids can be substituted or unsubstituted. Exemplary substituents include hydroxyl, halide, methyl, ethyl, propyl, isopropyl, butyl, and pentyl groups. Desirably, the fatty acid acyl is 4, 7, 10, 13, 16, 19 docosahexanoyl.

As used herein, the term "hydroxyl protecting group" refers to the use of an organic group at the 11-hydroxy position, other than mesylate and triflate, during the reduction of a compound of formula II to form a compound of formula III. Any hydroxyl protecting group known in the art can be used, including without limitation, ethers, such as methyl, methoxymethyl, methoxyethoxymethyl, methylthiomethyl, benzyloxymethyl, tetrahydropyranyl, ethoxyethyl, benzyl, 2-napthylmethyl, O-nitrobenzyl, P-nitrobenzyl, P-methoxybenzyl, 9-phenylxanthyl, trityl (including methoxy-trityls), and silyl ethers; esters; and amides. The hydroxyl protecting group can be chosen such that selective conditions (e.g., acidic conditions, basic conditions, catalysis by a nucleophile, catalysis by a lewis acid, or hydrogenation) are required to remove the protecting group, exclusive of altering other moieties in the molecule. The conditions required for the addition of protecting groups to alcohol functionalities and the conditions required for their removal are provided in detail in T. W. Green and P. G. M. Wuts, Protective Groups in Organic Synthesis ($2^{nd}$ Ed.), John Wiley & Sons, 1991 and P. J. Kocienski, Protecting Groups, Georg Thieme Verlag, 1994.

As used herein, the term "amine protecting group" refers to the use of an organic group at the amine position during the reduction of a compound of formula II to form a compound of formula III. Any amine protecting group known in the art can be used, including without limitation, carbamates, such as tert-butyl, benzyl, 2,2,2-trichloroethyl, 2-trimethylsilylethyl, 9-fluorenylmethyl, allyl, and m-nitrophenyl; amides, such as formamides, acetamides, trifluoroacetamides, sulfonamides, trifluoromethanesulfonyl amides, trimethylsilylethanesulfonamides, and tert-butylsulfonyl amides; benzylamine, and silylamines, such as trimethylsilylamine. The amine protecting group can be chosen such that selective conditions (e.g., acidic conditions, basic conditions, catalysis by a nucleophile, catalysis by a lewis acid, or hydrogenation) are required to remove the protecting group, exclusive of altering other moieties in the molecule. The conditions required for the addition of protecting groups to alcohol functionalities and the conditions required for their removal are provided in detail in T. W. Green and P. G. M. Wuts, Protective Groups in Organic Synthesis ($2^{nd}$ Ed.), John Wiley & Sons, 1991 and P. J. Kocienski, Protecting Groups, Georg Thieme Verlag, 1994.

The invention features synthetic methods for derivatives of R(−)-2-methoxy-11-hydroxyaporphines and their use for the treatment of diseases, such as Parkinson's disease, sexual dysfunction, and depressive disorders.

Other features and advantages of the invention will be apparent from the following Detailed Description, and the claims.

DETAILED DESCRIPTION

We have made compounds that are useful for the treatment of Parkinson's disease, sexual dysfunction, and depressive disorders.

The compounds are described by formula I below.

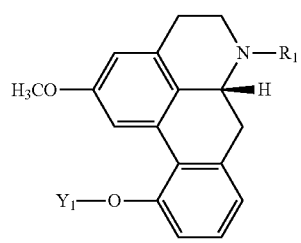

(I)

In formula I, $Y_1$ is H, C(O)—$R_3$, C(O)—O—$R_3$, C(O)—$NR_3R_4$, P(O)(OH)—O—$R_3$, C(S)—$R_3$, C(S)—O—$R_3$, C(S)—$NR_3R_4$, or fatty acid acyl; $R_1$ is H, $C_{1-4}$ alkyl, $C_{2-4}$ alkenyl, or $C_{2-4}$ alkynyl; and each of $R_3$ and $R_4$ is, independently, selected from H, $C_{1-12}$ alkyl, $C_{2-12}$ alkenyl, $C_{2-12}$ alkynyl, $C_{2-6}$ heterocyclyl, $C_{6-12}$ aryl, $C_{7-14}$ alkaryl, $C_{3-10}$ alkheterocyclyl, and $C_{1-7}$ heteroalkyl, or $R_3$ and $R_4$ together form a heterocyclic ring containing at least one nitrogen atom. In certain embodiments, $Y_1$ is H, C(O)—$R_3$, or C(O)—NH$R_4$;

$R_1$ is H, H, $CH_3$, $CH_2CH_3$, $CH_2CH_2CH_3$, $CH_2CH_2$=$CH_2$, $CH_2C$≡$CH$, $CH_2CH_2CH_2CH_3$, or cyclopropylmethyl; and each of $R_3$ and $R_4$ is, independently, selected from H, $C_{1-12}$ alkyl, $C_{2-12}$ alkenyl, and $C_{2-12}$ alkynyl.

These compounds can be prepared as described in the Examples.

Assays

To determine their affinity for dopamine receptors, compounds of the invention can be characterized in radioligand receptor binding assays, as described in Example 10.

The in vivo potency and bioavailability of R(-)-2-methoxy-11-hydroxyaporphine derivatives can be determined by administering the compound to an animal and monitoring the stimulation of motor activity as described in Example 11.

A symptom of clinical depression that can be modeled in rats is despair, a feeling of hopelessness. Symptoms of despair can be induced in rats using the forced swim test (FST), a highly validated model used to study antidepressant treatments. The efficacy of R(-)-2-methoxy-11-hydroxyaporphine derivatives for the treatment of depressive disorders can be assessed using the forced swim test. The FST is a two day procedure in which rats swim under conditions in which escape is not possible. On the first day, the rats are forced to swim for 15 minutes. The rats initially search for an escape from the water, but eventually adopt a posture of immobility in which they make only the movements necessary to keep their heads above water. Upon re-testing one day later, latencies to become immobile (an indicator of how rapidly the rats "give up" in response to a familiar stressor) are decreased, which is inferred as despair. Standard antidepressants such as imipramine (IMI) and fluoxetine (FLX) extend latencies to become immobile. Drug efficacy in this animal model is predictive of antidepressant efficacy in humans. The FST has been described by Mague et al., *J. Pharmacol. Exp. Ther.* 305:323 (2003).

Therapy

Representative examples of diseases and conditions treatable using compounds of the present invention are as listed hereinabove, and include, but are not limited to, Parkinson's disease, sexual dysfunction, and depressive disorders, such as major depression and bipolar disorder.

Formulations may be in the form of liquid solutions or suspensions; for oral administration, formulations may be in the form of tablets or capsules; and for intranasal formulations, in the form of powders, nasal drops, or aerosols.

Methods well known in the art for making formulations are found, for example, in "Remington: The Science and Practice of Pharmacy" (20th ed., ed. A. R. Gennaro A R., 2000, Lippincott Williams & Wilkins). Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Nanoparticulate formulations (e.g., biodegradable nanoparticles, solid lipid nanoparticles, liposomes) may be used to control the biodistribution of the compounds. Other potentially useful parenteral delivery systems include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycolate and deoxycholate, or may be oily solutions for administration in the form of nasal drops, or as a gel. The concentration of the compound in the formulation will vary depending upon a number of factors, including the dosage of the drug to be administered, and the route of administration.

The compound may be optionally administered as a pharmaceutically acceptable salt, such as a non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acid such as hydrochloric acid, hydrobromic acid, sulfuric acid phosphoric acid, or the like. Metal complexes include calcium, zinc, iron, and the like.

Administration of compounds in controlled release formulations is useful where the compound of formula I has (i) a narrow therapeutic index (e.g., the difference between the plasma concentration leading to harmful side effects or toxic reactions and the plasma concentration leading to a therapeutic effect is small; generally, the therapeutic index, TI, is defined as the ratio of median lethal dose ($LD_{50}$) or median toxic dose ($TD_{50}$) to median effective dose ($ED_{50}$); (ii) a narrow absorption window in the gastro-intestinal tract; or (iii) a short biological half-life, so that frequent dosing during a day is required in order to sustain the plasma level at a therapeutic level.

Many strategies can be pursued to obtain controlled release in which the rate of release outweighs the rate of metabolism of the therapeutic compound. For example, controlled release can be obtained by the appropriate selection of formulation parameters and ingredients, including, e.g., appropriate controlled release compositions and coatings. Examples include single or multiple unit tablet or capsule compositions, oil solutions, suspensions, emulsions, microcapsules, microspheres, nanoparticulate formulations, patches, and liposomes.

Formulations for oral use include tablets containing the active ingredient(s) in a mixture with non-toxic pharmaceutically acceptable excipients. These excipients may be, for example, inert diluents or fillers (e.g., sucrose and sorbitol), lubricating agents, glidants, and antiadhesives (e.g., magnesium stearate, zinc stearate, stearic acid, silicas, hydrogenated vegetable oils, or talc).

Formulations for oral use may also be provided as chewable tablets, or as hard gelatin capsules wherein the active ingredient is mixed with an inert solid diluent, or as soft gelatin capsules wherein the active ingredient is mixed with water or an oil medium.

Formulations for oral use also include rapidly disintegrating or dissolving dosage forms, also known as fast dissolve, fast or rapid melt, and quick disintegrating dosage forms. These dosage forms dissolve or disintegrate rapidly in the patient's mouth without chewing or the need for water within a short time frame. Because of their ease of administration, such compositions are particularly useful for the specific needs of pediatrics, geriatrics, and patients with dysphagia.

The formulations can be administered to patients in therapeutically effective amounts. For example, an amount is administered which prevents, reduces, or eliminates the symptoms of Parkinson's disease, sexual dysfunction, or depression, respectively. Typical dose ranges are from about 0.001 mg/kg to about 2 mg/kg of body-weight per day. Desirably, a dose of between 0.001 mg/kg and 1 mg/kg of body weight, or 0.005 mg/kg and 0.5 mg/kg of body weight, is administered. The exemplary dosage of drug to be administered is likely to depend on such variables as the type and extent of the condition, the overall health status of the particular patient, the formulation of the compound, and its route of administration. Standard clinical trials may be used to optimize the dose and dosing frequency for any particular compound.

The compounds of the invention may also be administered by a dose escalating method of acclimatization as described in U.S. Pat. No. 5,994,363 thereby ameliorating potential adverse effects. Furthermore, potential adverse effects can be ameliorated by administering R(−)-2-methoxy-11-hydroxyaporphine compounds of the invention in combination with an anti-emetic agent, such as nicotine, lobeline sulfate, pipamazine, oxypendyl hydrochloride, ondansetron, buclizine hydrochloride, cyclizine hydrochloride, dimenhydrinate, scopolamine, metopimazine, diphenhydramine, or diphenidol hydrochloride.

The following examples are put forth so as to provide those of ordinary skill in the art with a complete disclosure and description of how the methods and compounds claimed herein are performed, made, and evaluated, and are intended to be purely exemplary of the invention and are not intended to limit the scope of what the inventors regard as their invention.

Melting points were measured with a Thomas Hoover Capillary Melting Point Apparatus, and are uncorrected. $^1$H and $^{13}$C NMR spectra were obtained on Varian 300 spectrometer, chemical shifts are reported in ppm ($\delta$) from internal TMS and coupling constants (J) are measured in Hz. Thin layer chromatography was performed on 0.2-mm Kieselgel 60F 254 silica gel plastic sheets (EM Science, Newark). GC-MS analyses were performed with a Hewlett-Packard 5890 (Wilmington, Del.) gas chromatograph interfaced with a Hewlett-Packard 5972 mass selective detector. Element analyses, performed by Atlantic Microlabs, Atlanta, Ga., were within ±0.4% of theoretical values. Flash chromatography was used for the routine purification of reaction products.

Natural and synthetic aporphine alkaloids are of interest for their biological activity particularly for their dopaminergic activity (Zhang et al., J. Med. Chem. 50:171 (2007); and Zhang et al., Chem. Rev. 2007, 107:274 (2007)). Novel 2-substituted R(−)-apomorphine analogs have been prepared in several laboratories including ours (see structures below). It was observed that substituents in the 2-position of aporphines modulate dopaminergic $D_2$ activity and selectivity (Gao et al., J. Med. Chem. 33:1800 (1990), Ramsby et al., J. Med. Chem. 32:1198 (1989), Baldessarini et al., Neuropharmacology 30:97 (1991), and Sondergaard et al., Org. Biomol. Chem. 3:4077 (2005)). Dopamine receptor affinity studies showed that R(−)-2-hydroxy-N-n-propylnorapomorphine (R(−)-2-OH-NPA) and R(−)-2-methoxy-N-n-propylnorapomorphine (R(−)-2-OMe-NPA 1c) were among the most potent and highly selective agonists for the $D_2$ receptor ((Gao et al., J. Med. Chem. 33:1800 (1990)). The selectivity and binding affinity of apomorphine was also modified by the elimination of the 10-hydroxy group in apomorphine (Csutoras et al., Bioorg. Med. Chem. 12:3553 (2004), Neumeyer et al., J. Med. Chem. 17:1090 (1974), Neumeyer et al., J. Med. Chem. 24:1440 (1981), Ram et al., J. Org. Chem. 47:4372 (1982), Zhang et al., Org. Lett. 7:3239 (2005)). These investigations led to R(−)-11-hydroxy-N-n-propylnoraporphine (R(−)-11-OH—NPa 2) a compound displaying even higher affinity and selectivity for $D_2$ receptor than apomorphine ((Gao et al., J. Med. Chem. 33:1800 (1990)). Based on these findings, we investigated the synthesis of a compound with the combination of a 2-OCH$_3$ group and elimination of the 10-hydroxyl group such as 3.

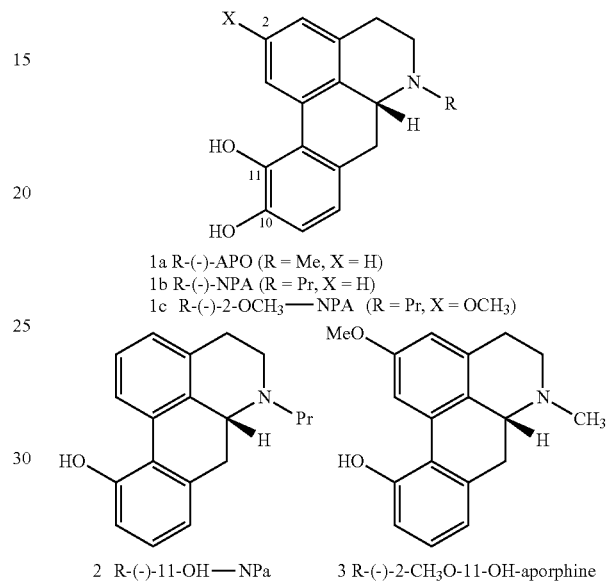

1a R-(−)-APO (R = Me, X = H)
1b R-(−)-NPA (R = Pr, X = H)
1c R-(−)-2-OCH$_3$—NPA (R = Pr, X = OCH$_3$)

2 R-(−)-11-OH—NPa

3 R-(−)-2-CH$_3$O-11-OH-aporphine

Initially we speculated that if we could prepare the corresponding rearrangement precursor 4, then the target compound 3 should be obtained by the rearrangement of 4 under acid conditions (see Scheme 1). However, several attempts to convert the enone 10 to the key intermediate 4 failed. These conditions included Me$_2$SO$_4$/KOtBu/NMP, Me$_2$SO$_4$/KOtBu/THF, Me$_2$SO$_4$/KOtBu/HMPA and Me$_2$SO$_4$/KOtBu/18-crown-6/HMPA (U.S. Pat. Nos. 6,790,959 and 6,090,943; Coop et al., Heterocycles 49:43 (1998)). The conversion of the enone 10 to the enol ester 11 (PCT Publ. No. WO9902529) or oxidation of the enol methyl ether 12 also failed (Rapoport et al., J. Med. Chem. 18:1074 (1975)).

Scheme 1

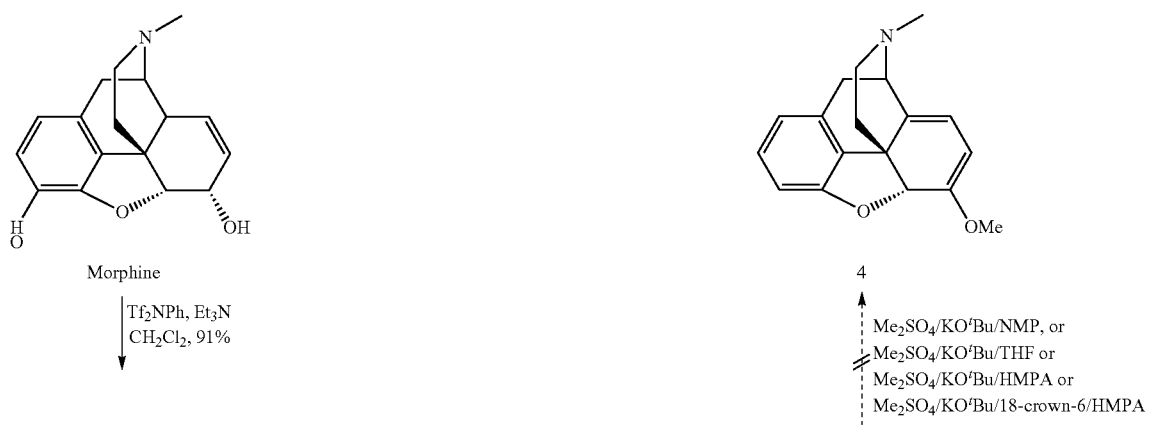

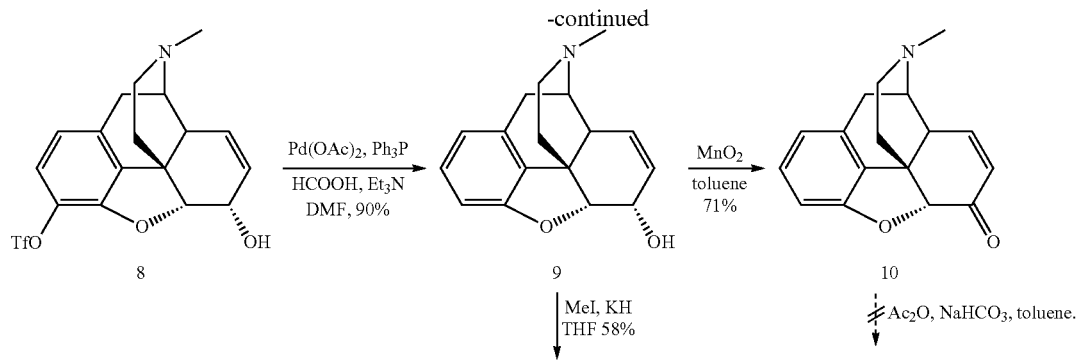

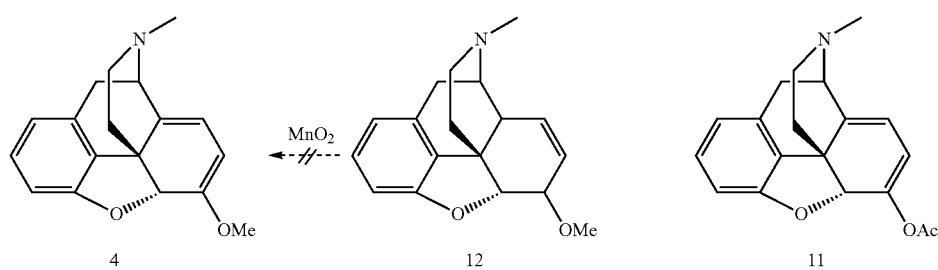

Alternatively, O-triflation of oripavine (oripavine could also be prepared from thebaine as described in Coop et al., *J. Org. Chem.* 61:6774 (1996); and Janetka et al., *J. Org. Chem.* 63:4392 (1998)) with PhNTf₂ yielded the compound 6 (see Scheme 2). We speculated that further reduction of triflate 6 would yield the rearrangement precursor 4. However, classic reduction condition (Pd(OAc)₂, Ph₃P, HCOOH, Et₃N, DMF) decomposed the starting material even at room temperature. Using other palladium sources (Pd(Ph₃P)₄, Pd(Ph₃P)₂Cl₂), phosphorous ligand (DPPP, DPPF) and base (Bu₃N) all led to decomposition (Cacchi et al., *Tetrahedron Lett.* 27:5541 (1986); Chen et al., *J. Chem. Soc. Chem. Commun.* 1452 (1986); Cabri et al., *J. Org. Chem.* 55:350 (1990); and Saa et al., *J. Org. Chem.* 55:991 (1990)). The procedure reported recently by Sajiki using Pd/C and Mg in the presence of NH₄OAc also failed in this reduction (Sajiki et al., *Org. Lett.* 8:987 (2006)).

We then turned our attention to the acid catalyzed rearrangement of compound 6 to form compound 7, followed by reduction to form compound 3. Acid catalyzed rearrangement of the triflate 6 gave the aporphine triflate 7 in 56% yield (Scheme 2). Palladium catalyzed reduction of triflate 7 under previously reported standard conditions (Pd(OAc)₂, Ph₃P, HCOOH, Et₃N, DMF) furnished the catecholaporphine 8 in 56% yield but only 5% yield of desired compound 3. Using other palladium sources and phosphorous ligands led to similar results. Reduction of the 11-hydroxy acetic ester derivative of 7 also led to the catecholaporphine 8. Fortunately using Pd/C catalyzed with Mg in the presence of NH₄OAc was successful in this reduction. After several attempts, it was found that compound 3 could be obtained in 75% isolated yield when 20% weight Pd/C, 3.0 equal molar Mg and 5.0 equal molar NH₄OAc was used in methanol at room temperature. Further details are provided in the Examples.

Scheme 2

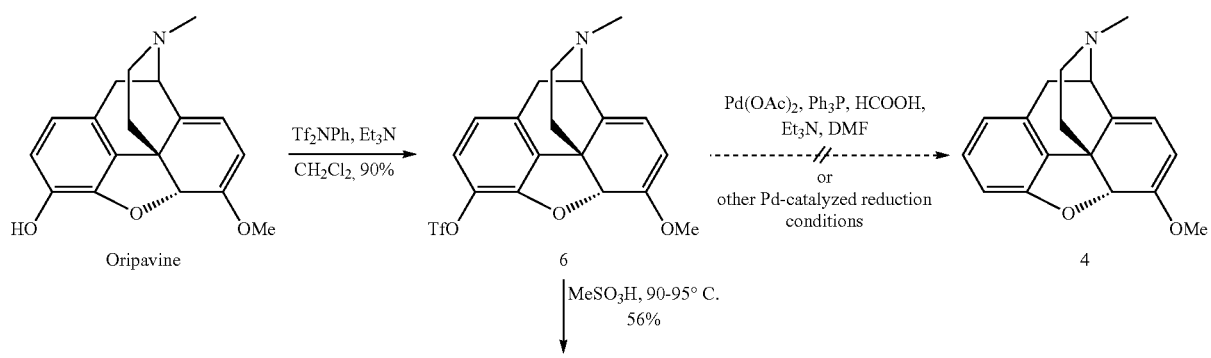

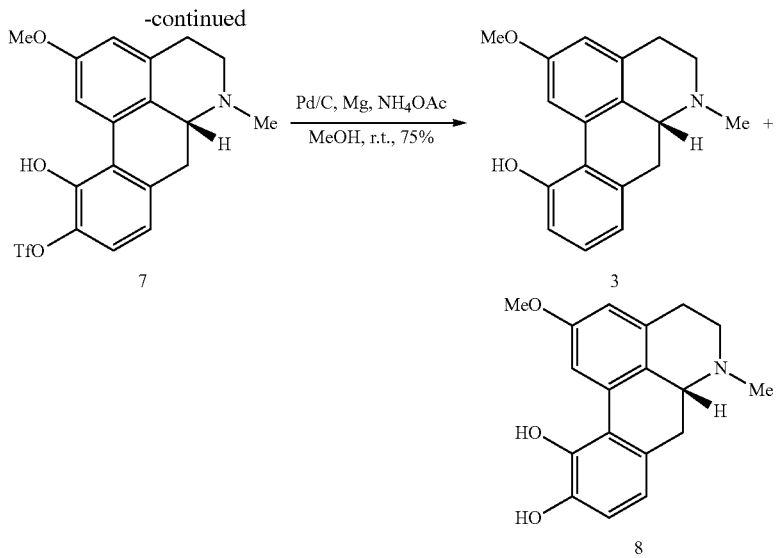

EXAMPLE 1

Synthesis of 3-O-[(Trifluoromethyl)sulfonyl]oripavine (6)

Under nitrogen, N-phenyltrifluoromethanesulfonimide (4.28 g, 11 mmol) was added to the mixture of oripavine (2.97 g, 10 mmol) and triethylamine (2.1 mL, 15 mmol) in $CH_2Cl_2$ (50 mL). The resulting mixture was stirred at room temperature for 3 hours. The reaction mixture was washed with 30 mL water and 30 mL brine. The organic layer was dried with anhydrous $Na_2SO_4$, and the solvent was evaporated. The residue was dissolved in ether (60 mL) and extracted with 1 M HCl (4×50 mL). The combined acidic layer was basified with ammonium hydroxide, and the mixture was extracted with $CH_2Cl_2$ (3×50 mL). The organic layer was washed with brine (80 mL), dried with anhydrous $Na_2SO_4$. The solvent was evaporated. The residue was purified with a short silica gel column chromatography, eluting with $CH_2Cl_2$:MeOH (20:1) to yield 3.9 g of compound 6 (90%). mp 143-145° C.; $^1H$ NMR (300 MHz, $CDCl_3$) δ 6.94 (d, J=8.4 Hz, 1H), 6.66 (d, J=8.7 Hz, 1H), 5.59 (d, J=6.3 Hz, 1H), 5.39 (s, 1H), 5.06 (d, J=6.6 Hz, 1H), 3.64 (d, J=6.9 Hz, 1H), 3.61 (s, 3H), 3.34 (d, J=18.6 Hz, 1H), 2.82-2.63 (m, 3H), 2.46 (s, 3H), 2.24 (ddd, J=12.6, 5.1 and 5.1 Hz, 1H), 1.75 (dd, J=12.6 and 1.8 Hz, 1H); $^{13}C$ NMR (75 MHz, $CDCl_3$) δ 152.0, 147.85, 136.0, 135.7, 131.2, 131.1, 121.5, 119.7, 118.7 (q, J=318 Hz), 112.2, 96.3, 90.8, 60.3, 55.0, 45.9, 45.7, 42.3, 36.6, 29.8.

EXAMPLE 2

Synthesis of 2-Methoxy-10-O-[(trifluoromethyl)sulfonyl]-11-hydroxyaporphine (7)

Triflate 6 (2.4 g, 5.6 mmol) was dissolved in 99% methanesulfonic acid (15 mL, 232 mmol), under nitrogen at room temperature. The resulting mixture was stirred for 30 min at 90° C., and then cooled to room temperature. Ice-water (50 mL) was added and the mixture was basified with ammonia hydroxide, extracted with $CH_2Cl_2$ (3×50 mL). The organic layer was washed with brine (50 mL), dried with anhydrous $Na_2SO_4$. The solvent was evaporated. The residue was purified with silica gel column chromatography, eluting with $CH_2Cl_2$:MeOH (50:1) and recrystallized from methanol to yield 1.35 g of compound 7 as white solid (56%). mp 168-170° C. $^1H$ NMR (300 MHz, DMSO-$d_6$) δ 7.66 (br, 1H), 7.24 (d, J=8.1 Hz, 1H), 7.18 (d, J=2.7 Hz, 1H), 6.95 (d, J=8.1 Hz, 1H), 6.71 (dd, J=12.9 and 2.7 Hz, 1H), 3.75 (s, 3H), 3.25-2.67 (m, 6H), 2.44 (s, 3H), 2.38-2.16 (m, 1H). Anal. calcd. for $C_{19}H_{18}F_3NO_5S$: C, 53.14; H, 4.23; N, 3.26. Found: C, 53.26; H, 4.23; N, 3.30.

EXAMPLE 3

Synthesis of 2-Methoxy-11-hydroxyaporphine (3)

Under nitrogen Mg (36 mg, 1.5 mmol) and $NH_4OAc$ (193 mg, 2.5 mmol) was added to the mixture of triflate 7 (215 mg, 0.5 mmol) and 10% Pd/C (44 mg) in MeOH (15 mL) at room temperature. The resulting mixture was stirred at room temperature for 24 hours and filtered with celite. The residue was washed with MeOH (2×20 mL). The filtrate was evaporated to dryness and dissolved in 100 mL $CH_2Cl_2$. The solution was washed with 30 mL 10% ammonium hydroxide and 50 mL brine. The organic layer was dried with anhydrous $Na_2SO_4$ and evaporated in vacuo to dryness. The residue was purified with column ($CH_2Cl_2$:MeOH=100:1) and recrystallized from $CH_2Cl_2$ to yield 105 mg colorless solid (75%). mp 214-215° C.; $^1H$ NMR (300 MHz, $CDCl_3$) δ 7.61 (d, J=2.7 Hz, 1H), 7.08 (dd, J=7.5 and 7.5 Hz, 1H), 6.85 (d, J=7.2 Hz, 1H), 6.76 (d, J=8.1 Hz, 1H), 6.61 (d, J=2.7 Hz, 1H), 3.80 (s, 3H), 3.25-3.02 (m, 4H), 2.76-2.49 (m, 3H), 2.55 (s, 3H); $^{13}C$ NMR (75 MHz, $CDCl_3$) δ 158.0, 152.8, 138.5, 134.5, 132.4, 128.2, 127.4, 121.1, 120.7, 115.6, 111.9, 111.1, 61.8, 55.2, 53.1, 43.9, 35.3, 29.4; m/z 281 (M+). Anal. calcd. for $C_{18}H_{19}NO_2$: C, 76.84; H, 6.81; N, 4.98. Found: C, 76.65; H, 6.85; N, 5.06.

EXAMPLE 4

Synthesis of 2-Methoxy-11-hydroxy-N-ethylnoraporphine(13)

2-Methoxy-11-hydroxy-N-ethylnoraporphine was prepared as described in Scheme 3.

Scheme 3

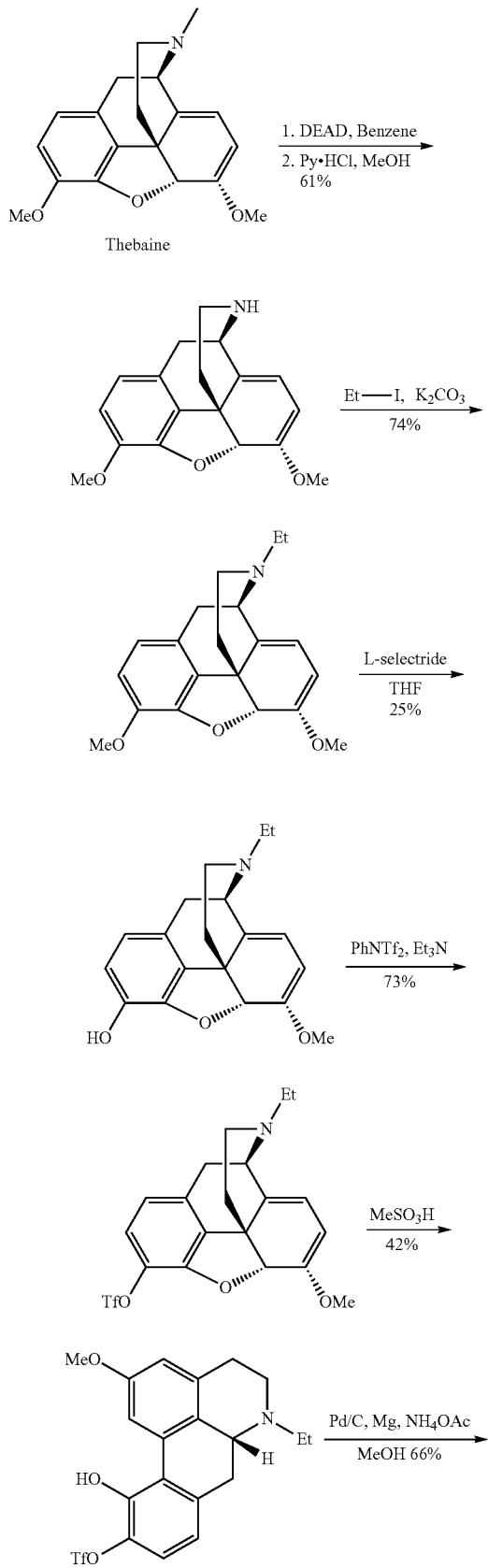

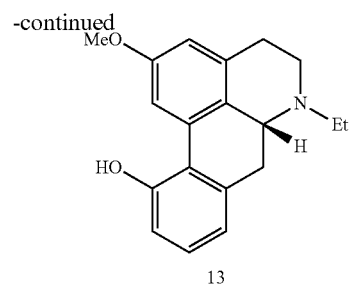

Preparation of Northebaine:

The mixture of thebaine (12 g, 38.5 mmol) and DEAD (8.7 g, 7.8 mL, 50 mmol) in benzene was refluxed for 3 days. The mixture was evaporated and MeOH (100 mL) was added to the system followed by pyridine hydrochloride (7.08 g, 61.6 mmol) and the mixture was stirred overnight. The solvent was evaporated in vacuo, producing a brown gum. MeOH (5 mL) and 200 mL EtOAc were added to the gum, stirred for 2 days, and mixture filtered to yield a white solid (25-34%). mp 270-272° C. The product identity was confirmed by $^1$H NMR (CD$_3$OD).

Preparation of N-ethylnorthebaine:

A mixture of ethyliodide (1.87 g, 12 mmol, 1.0 mL), K$_2$CO$_3$ (3.036 g, 22 mmol) and northebaine hydrochloride (3.3 g, 10 mmol) in EtOH (70 mL) was refluxed for overnight. Ethanol was removed in vacuo. Water (50 mL) was added into the residue and extracted with EtOAc (3×30 mL). The combined organic layer was washed with brine (50 mL), dried with Na$_2$SO$_4$ and evaporated in vacuo. The residue was purified with silica gel column (CH$_3$OH:CH$_2$Cl$_2$=1:100 to 1:20) to produce the product (2.40 g, 74% yield). $^1$H NMR (300 MHz, CDCl$_3$) δ 6.66 (d, J=8.4 Hz, 1H), 6.60 (d, J=8.1 Hz, 1H), 5.57 (d, J=6.6 Hz, 1H), 5.30 (s, 1H), 5.03 (d, J=6.3 Hz, 1H), 3.85 (s, 3H), 3.77 (d, J=7.2 Hz, 1H), 3.60 (s, 3H), 3.30 (d, J=17.7 Hz, 1H), 2.82-2.74 (m, 3H), 2.70-2.62 (m, 2H), 2.19 (m, 1H), 1.74 (dt, J=12.0 and 2.7 Hz, 1H), 1.16 (t, J=7.2 Hz, 3H); $^{13}$C NMR. (75 MHz, CDCl$_3$) δ 152.5, 144.6, 142.8, 133.4, 131.9, 127.5, 119.2, 112.7, 111.9, 95.8, 89.1, 58.4, 56.3, 54.9, 47.7, 46.4, 43.6, 36.6, 30.3, 12.8.

Preparation of 2-O-demethyl-N-ethylnorthebaine:

A mixture of 2.4 g N-ethylnorthebaine and 15 mL L-selectride (1M in THF) was heated under reflux for 30 minutes. The mixture was cooled to room temperature and poured onto 50 mL ice-water. 10 mL 1 N NaOH was added. The mixture was extracted with CH$_2$Cl$_2$ (3×50 mL). At 0-5° C., the aqueous phase was acidified to pH=1-2 with 10% HCl and then basified to pH=9-10 with NH$_4$OH. The mixture was extracted with CH$_2$Cl$_2$ (3×50 mL). The combined organic layer was washed with brine (100 mL), dried with sodium sulfate and concentrated in vacuo. The residue was purified by silica gel column chromatography (CH$_3$OH:CH$_2$Cl$_2$=1:10 to 1:5) to produce the product (570 mg, 25% yield). mp 130-132° C. $^1$H NMR (300 MHz, CDCl$_3$) δ 6.63 (d, J=8.1 Hz, 1H), 6.53 (d, J=8.1 Hz, 1H), 5.57 (d, J=6.6 Hz, 1H), 5.27 (s, 1H), 5.05 (d, J=6.3 Hz, 1H), 3.83 (d, J=6.9 Hz, 1H), 3.59 (s, 3H), 3.29 (d, J=18.3 Hz, 1H), 2.88-2.66 (m, 5H), 2.20 (m, 1H), 1.70 (d, J=12.3 Hz, 1H), 1.14 (t, J=7.2 Hz, 3H); $^{13}$C NMR (75 MHz, CDCl$_3$) δ 152.2, 143.0, 138.8, 133.0, 132.3, 126.5, 119.7, 116.5, 111.9, 96.2, 89.2, 58.3, 54.9, 47.4, 46.7, 43.3, 36.1, 30.9, 12.5.

Preparation of 3-O-((trifluoromethyl)sulfonyl)-N-ethylnorthebaine:

To a solution of 570 mg (1.83 mmol) 2-O-demethyl-N-ethylnorthebaine and Et$_3$N (277 mg, 0.38 mL, 2.7 mmol) in 70 mL CH$_2$Cl$_2$ at 0-5° C. was added Tf$_2$NPh (718 mg, 2.0 mmol). After the addition, the mixture was slowly warmed to room temperature and stirred overnight. The reaction was monitored by TLC (CH$_3$OH:CH$_2$Cl$_2$=1:10), which showed no starting material remaining. The reaction mixture was quenched with an aqueous saturated solution of KHCO$_3$ and extracted with CH$_2$Cl$_2$ (2×100 mL). The combined organic layer was washed with brine (100 mL), dried with sodium sulfate and concentrated in vacuo. The residue oil was purified by column chromatography (CH$_3$OH:CH$_2$Cl$_2$=1:100 to 1:20) to produce the product (590 mg, 73% yield). $^1$H NMR (300 MHz, CDCl$_3$) δ 6.93 (d, J=8.4 Hz, 1H), 6.65 (d, J=8.7 Hz, 1H), 5.56 (d, J=6.6 Hz, 1H), 5.38 (s, 1H), 5.06 (d, J=6.4 Hz, 1H), 3.72 (d, J=7.2 Hz, 1H), 3.61 (s, 3H), 3.30 (d, J=18.6 Hz, 1H), 2.77-2.68 (m, 3H), 2.53-2.49 (m, 2H), 2.23 (m, 1H), 1.74-1.68 (m, 1H), 1.58-1.51 (m, 2H), 1.15 (t, J=7.2 Hz, 3H).

Preparation of R(-)-2-methoxy-10-((trifluoromethyl)sulfonyl)oxy-11-hydroxy-N-ethyl-noraporphine:

A mixture of 3-O-((trifluoromethyl)sulfonyl)-N-ethyl-northebaine (590 mg) in MeSO$_3$H (7 mL) was warmed up to 95° C. and stirred for 30 minutes.

After cooling to room temperature, the mixture was poured onto ice water and neutralized to pH=9-10 with ammonium hydroxide. The mixture was extracted with CH$_2$Cl$_2$ (3×50 mL). The combined organic layer was washed with brine, dried with Na$_2$SO$_4$, and evaporated in vacuo. The residue was purified by silica gel column (CH$_3$OH:CH$_2$Cl$_2$=1:40 to 1:20) to produce the product (245 mg, 42% yield) as a pale white solid. mp 178-180° C. (Dec). $^1$H NMR (300 MHz, DMSO-d$_6$) δ 7.64 (s, br, 1H), 7.24 (dd, J=7.8 and 5.1 Hz, 1H), 7.16 (d, J=2.4 Hz, 1H), 6.94 (d, J=8.1 Hz, 1H), 6.70 (dd, J=12.9 and 2.4 Hz, 1H), 3.74 (s, 3H), 3.23-2.88 (m, 6H), 2.70 (m, 1H), 2.38-2.11 (m, 2H), 1.05 (t, J=5.7 Hz, 3H).

Preparation of 2-Methoxy-11-hydroxy-N-ethylnoraporphine(13):

Mg (30 mg) and NH$_4$OAc (154 mg) was added to a mixture of R(-)-2-methoxy-10-((trifluoromethyl)sulfonyl)oxy-11-hydroxy-N-butylnoraporphine (180 mg) and 10% Pd/C (36 mg) in MeOH (20 mL). The resulted mixture was stirred at room temperature for 24 hours and filtered over celite. The filtrate was evaporated to dryness and dissolved in CH$_2$Cl$_2$. The solution was washed with 10% NH$_4$OH and brine, dried with Na$_2$SO$_4$, and evaporated in vacuo to dryness. The residue was purified by column chromatography (CH$_2$Cl$_2$:MeOH=100:1) to produce the product 13 (79 mg). The product was converted to the HCl salt with 1N HCl in ether. mp 248-250° C. (HCl salt, Dec). The free base was checked with EI MS, $^1$H NMR and $^{13}$C NMR. MS (EI): m/z 296(M+H)$^+$. $^1$H NMR (300 MHz, CDCl$_3$) δ 7.68 (d, J=2.7 Hz, 1H), 7.01 (t, J=7.8 Hz, 1H), 6.79 (d, J=7.2 Hz, 1H), 6.70 (d, J=8.1 Hz, 1H), 6.58 (d, J=2.4 Hz, 1H), 3.78 (s, 3H), 3.35 (d, J=13.5 Hz, 1H), 3.21-3.05 (m, 4H), 2.76-2.50 (m, 4H), 1.18 (t, J=6.9 Hz, 3H); $^{13}$C NMR (75 MHz, CDCl$_3$) δ 157.8, 153.0, 138.3, 134.4, 132.8, 128.1, 127.3, 121.2, 120.3, 115.6, 111.9, 111.4, 58.6, 55.2, 48.0, 47.7, 34.9, 29.1, 10.5. Anal. calcd. for C$_{19}$H$_{21}$NO$_2$.HCl..0.9H$_2$O: C, 65.71; H, 6.85; N, 4.03. Found: C, 65.94; H, 6.51; N, 4.05.

EXAMPLE 5

Synthesis of R(-)-2-Methoxy-11-hydroxy-N-butyl-noraporphine(14)

2-Methoxy-11-hydroxy-N-butylnoraporphine was prepared as described in Scheme 4 using conditions analogous to those provided in Example 4. Data on intermediates and the final product are provided below.

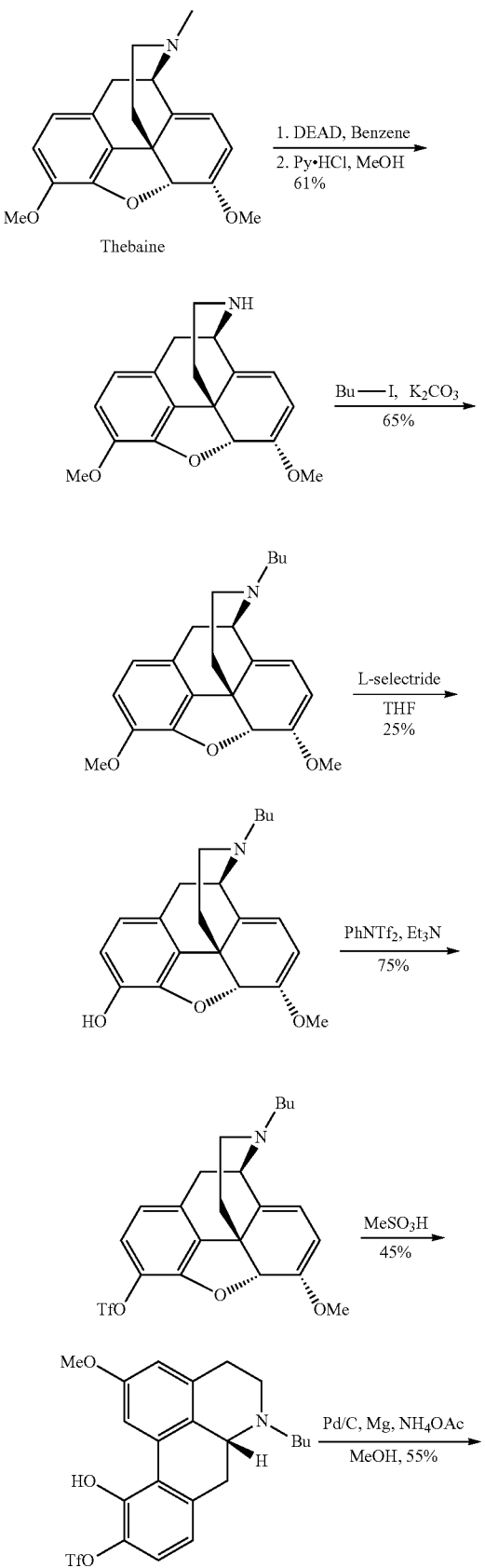

Scheme 4

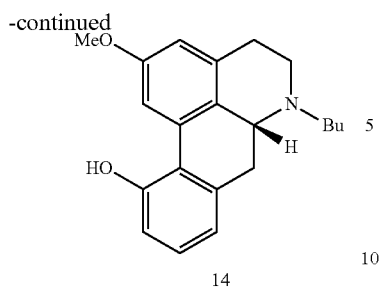

14

N-butylnorthebaine: ¹H NMR (300 MHz, CDCl₃) δ 6.65 (d, J=8.4 Hz, 1H), 6.59 (d, J=8.1 Hz, 1H), 5.54 (d, J=6.3 Hz, 1H), 5.29 (s, 1H), 5.03 (d, J=6.6 Hz, 1H), 3.84 (s, 3H), 3.71 (d, J=6.9 Hz, 1H), 3.59 (s, 3H), 3.28 (d, J=18.0 Hz, 1H), 2.85-2.66 (m, 3H), 2.57-2.52 (m, 2H), 2.18 (m, 1H), 1.70 (dt, J=12.3 and 2.7 Hz, 1H), 1.56-1.46 (m, 2H), 1.42-1.27 (m, 2H), 0.94 (t, J=7.2 Hz, 3H); ¹³C NMR (75 MHz, CDCl₃) δ 152.4, 144.6, 142.7, 133.5, 132.6, 127.8, 119.1, 112.7, 111.5, 95.9, 89.2, 58.8, 56.3, 54.9, 53.9, 46.5, 44.2, 36.9, 30.4, 30.0, 20.8, 14.1.

2-O-demethyl-N-butylnorthebaine: ¹H NMR (300 MHz, CDCl₃) δ 6.64 (d, J=7.8 Hz, 1H), 6.53 (d, J=8.4 Hz, 1H), 5.57 (d, J=6.6 Hz, 1H), 5.27 (s, 1H), 5.05 (d, J=6.3 Hz, 1H), 3.80 (d, J=6.6 Hz, 1H), 3.59 (s, 3H), 3.31 (d, J=18.0 Hz, 1H), 2.90-2.58 (m, 5H), 2.21 (m, 1H), 1.70 (d, J=12.6 Hz, 1H), 1.58-1.48 (m, 2H), 1.39-1.27 (m, 2H), 0.92 (t, J=7.5 Hz, 3H); ¹³C NMR (75 MHz, CDCl₃) δ 152.2, 143.0, 138.6, 132.9, 132.1, 126.6, 119.8, 116.4, 112.0, 96.3, 89.3, 58.9, 54.9, 53.5, 46.7, 43.8, 36.1, 31.0, 29.5, 20.8, 14.0.

3-O-((trifluoromethyl)sulfonyl)-N-butylnorthebaine: ¹H NMR (300 MHz, CDCl₃) δ6.93 (d, J=8.4 Hz, 1H), 6.65 (d, J=8.4 Hz, 1H), 5.57 (d, J=6.6 Hz, 1H), 5.38 (s, 1H), 5.06 (d, J=6.6 Hz, 1H), 3.73 (d, J=7.2 Hz, 1H), 3.61 (s, 3H), 3.30 (d, J=18.6 Hz, 1H), 2.77-2.68 (m, 3H), 2.57-2.52 (m, 2H), 2.23 (m, 1H), 1.74-1.69 (m, 1H), 1.56-1.46 (m, 2H), 1.42-1.28 (m, 2H), 0.94 (t, J=7.2 Hz, 3H); ¹³C NMR (75 MHz, CDCl₃) δ151.9, 147.8, 136.2, 136.0, 131.5, 131.2, 121.4, 119.7, 118.7 (J=322.5 Hz), 112.2, 96.3, 90.8, 58.4, 54.9, 53.9, 46.5, 43.9, 36.4, 30.9, 29.9, 20.7, 14.0.

R(−)-2-methoxy-10-((trifluoromethyl)sulfonyl)oxy-11-hydroxy-N-butylnoraporphine: mp 165-167° C. (Dec). ¹H NMR (300 MHz, CDCl₃) δ 7.55 (d, J=2.4 Hz, 1H), 7.07 (d, J=8.4 Hz, 1H), 6.82 (d, J=8.4 Hz, 1H), 6.55 (d, J=2.4 Hz, 1H), 3.75 (s, 3H), 3.29-2.85 (m, 5H), 2.67 (m, 1H), 2.53-2.41 (m, 3H), 1.58-1.48 (m, 2H), 1.40-1.32 (m, 2H), 0.96 (t, J=7.5 Hz, 3H); ¹³C NMR (75 MHz, CDCl₃) δ 158.0, 138.0, 135.0, 131.5, 130.6, 127.0, 126.6, 124.3, 120.3, 120.1, 118.3 (J=270.8 Hz), 112.6, 111.1, 58.6, 55.2, 53.4, 48.5, 34.5, 28.8, 27.9, 20.7, 14.0.

R(−)-2-Methoxy-11-hydroxy-N-butylnoraporphine (14): mp 218-220° C. (Dec). MS (EI): m/z 324 (M+H)⁺. ¹H NMR (300 MHz, DMSO-d₆) δ 11.02 (br, 1H), 10.16 (s, 1H), 7.91 (d, J=2.7 Hz, 1H), 7.11 (t, J=7.8 Hz, 1H), 6.93 (d, J=7.8 Hz, 1H), 6.86 (d, J=7.2 Hz, 1H), 6.76 (d, J=2.1 Hz, 1H), 4.29 (m, 1H), 3.82 (m, 1H), 3.77 (s, 3H), 3.53-3.27 (m, 3H), 3.16-2.88 (m, 4H), 1.80-1.72 (m, 2H), 1.45-1.33 (m, 2H), 0.95 (t, J=7.5 Hz, 3H); ¹³C NMR (75 MHz, DMSO-d₆) δ 158.2, 154.8, 135.3, 133.2, 131.4, 128.7, 121.1, 119.5, 119.3, 115.9, 113.7, 110.7, 59.0, 55.1, 52.6, 47.9, 31.1, 25.9, 24.7, 19.6, 13.6.

EXAMPLE 6

Synthesis of R(−)-2-Methoxy-11-hydroxy-N-propyl-noraporphine (15)

2-Methoxy-11-hydroxy-N-propylnoraporphine was prepared as described in Scheme 5 using conditions analogous to those provided in Example 4. Data on intermediates and the final product are provided below.

Scheme 5

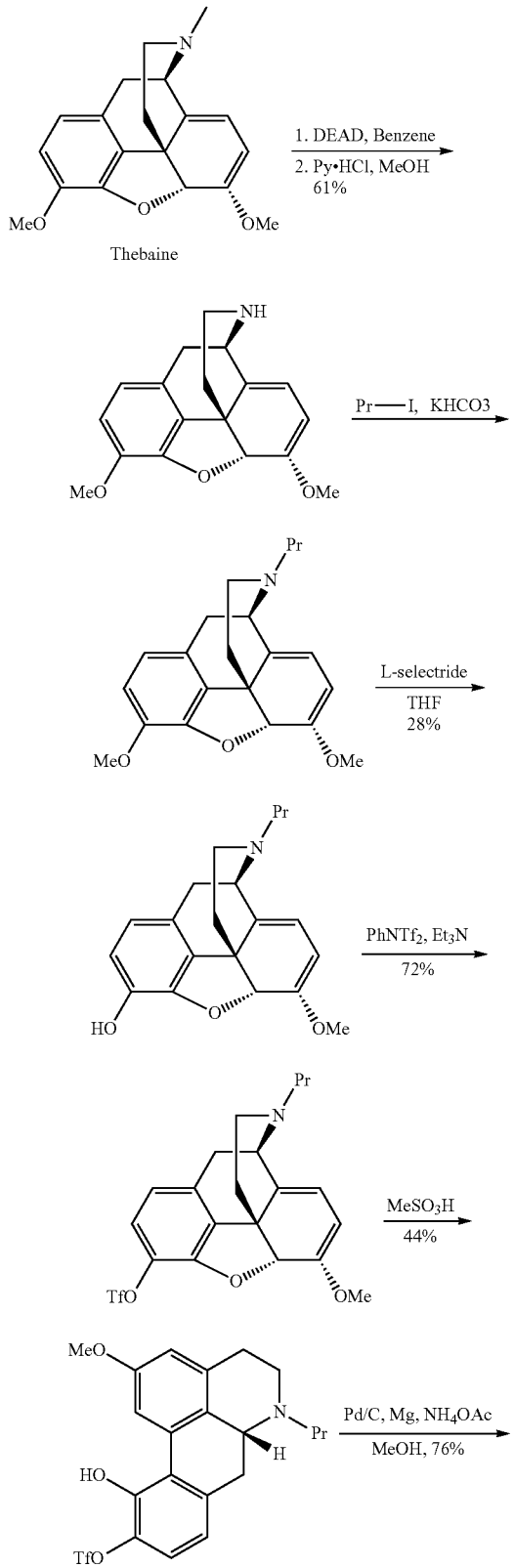

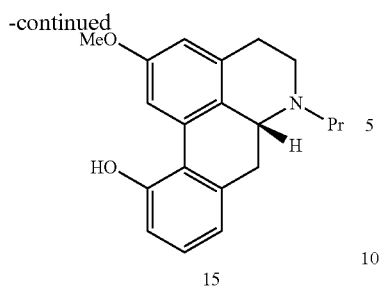

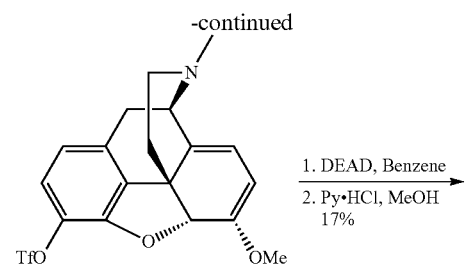

3-O-((trifluoromethyl)sulfonyl)-N-n-propylnorthebaine: $^1$H NMR (300 MHz, CDCl$_3$) δ 6.93 (d, J=8.1 Hz, 1H), 6.64 (d, J=8.4 Hz, 1H), 5.56 (d, J=6.6 Hz, 1H), 5.38 (s, 1H), 5.06 (d, J=6.4 Hz, 1H), 3.72 (d, J=7.2 Hz, 1H), 3.61 (s, 3H), 3.30 (d, J=18.6 Hz, 1H), 2.77-2.68 (m, 3H), 2.53-2.49 (m, 2H), 2.23 (m, 1H), 1.74-1.68 (m, 1H), 1.58-1.51 (m, 2H), 0.94 (t, J=6.9 Hz, 3H); $^{13}$C NMR (75 MHz, CDCl$_3$) δ 151.9, 147.8, 136.2, 136.0, 131.6, 131.2, 121.4, 119.7, 118.6 (J=319 Hz), 112.1, 96.3, 90.8, 58.5, 56.1, 55.0, 46.5, 43.8, 36.5, 31.0, 21.0, 11.9.

R(−)-2-methoxy-10-((trifluoromethyl)sulfonyl)oxy-11-hydroxy-N-n-propyl-noraporphine: mp 173-175° C. $^1$H NMR (300 MHz, DMSO-d$_6$) δ 7.65 (br, 1H), 7.25 (t, J=7.8 Hz, 1H), 7.18 (d, J=2.7 Hz, 1H), 6.95 (d, J=8.4 Hz, 1H), 6.72 (dd, J=12.3 and 2.4 Hz, 1H), 3.76 (s, 3H), 3.19-3.11 (m, 3H), 3.00-2.65 (m, 3H), 2.35-2.26 (m, 3H), 1.52 (m, 2H), 0.92 (t, J=7.2 Hz, 3H).

R(−)-2-methoxy-11-hydroxy-N-n-propylnoraporphine: mp 188-190° C. (Dec). The free base was checked with $^1$H NMR and $^{13}$C NMR. $^1$H NMR (300 MHz, CDCl$_3$) δ 7.68 (d, J=2.7 Hz, 1H), 7.01 (t, J=7.8 Hz, 1H), 6.80 (d, J=7.5 Hz, 1H), 6.68 (d, J=8.1 Hz, 1H), 6.57 (d, J=2.7 Hz, 1H), 3.78 (s, 3H), 3.35 (d, J=13.5 Hz, 1H), 3.21-3.05 (m, 3H), 2.92-2.89 (m, 1H), 2.74-2.68 (m, 1H), 2.59-2.43 (m, 3H), 1.65-1.57 (m, 2H), 0.95 (t, J=7.5 Hz, 3H); $^{13}$C NMR (75 MHz, CDCl$_3$) δ 157.8, 153.1, 138.5, 134.5, 132.8, 128.1, 127.6, 121.2, 120.3, 115.6, 111.9, 111.4, 59.2, 56.3, 55.2, 48.9, 35.1, 29.2, 19.0, 12.1. Anal. calcd. for C$_{20}$H$_{23}$NO$_2$.HCl.H$_2$O: C, 65.22; H, 7.02; N, 3.80. Found: C, 65.52; H, 6.65; N, 3.67.

EXAMPLE 7

Synthesis of R(−)-2-Methoxy-11-hydroxy-N-propargylnoraporphine (16)

2-Methoxy-11-hydroxy-N-propargylnoraporphine was prepared as described in Scheme 6 using conditions analogous to those provided in Example 4. Data on intermediates and the final product are provided below.

Scheme 6

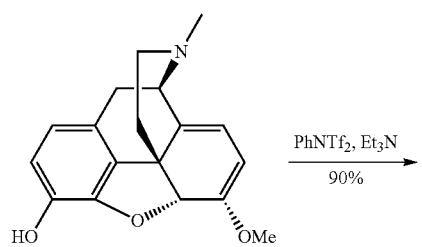

3-O-((trifluoromethyl)sulfonyl)-N-propargylnorthebaine: $^1$H NMR (300 MHz, CDCl$_3$) δ 6.94 (d, J=8.7 Hz, 1H), 6.67 (d, J=8.4 Hz, 1H), 5.62 (d, J=6.3 Hz, 1H), 5.38 (s, 1H), 5.06 (d, J=6.6 Hz, 1H), 3.94 (d, J=7.2 Hz, 1H), 3.62 (s, 3H), 3.45 (d, J=2.1 Hz, 2H), 3.36 (d, J=18.6 Hz, 1H), 2.95-2.81 (m, 3H), 2.31 (t, J=2.7 Hz, 1H), 2.23 (m, 1H), 1.73 (dt, J=12.6 and 2.4 Hz, 1H); $^{13}$C NMR (75 MHz, CDCl$_3$) δ 152.2, 147.8, 135.7, 135.6, 131.2, 130.1, 121.6, 119.8, 118.6 (q, J=319.1 Hz), 113.2, 96.2, 90.7, 79.9, 72.9, 58.2, 55.0, 46.2, 43.4, 43.0, 35.6, 32.0.

R(−)-2-methoxy-10-((trifluoromethyl)sulfonyl)oxy-11-hydroxy-N-propargylnoraporphine: $^1$H NMR (300 MHz, CDCl$_3$) δ 7.53 (d, J=2.4 Hz, 1H), 7.10 (d, J=8.4 Hz, 1H), 6.89 (d, J=8.4 Hz, 1H), 6.58 (d, J=2.4 Hz, 1H), 3.88 (m, 1H), 3.75 (s, 3H), 3.66-3.57 (m, 2H), 3.12-2.70 (m, 5H), 2.49 (t, J=13.8

Hz, 1H), 2.24 (t, J=2.1 Hz, 1H); $^{13}$C NMR (75 MHz, CDCl$_3$) δ 158.0, 144.7, 138.0, 137.6, 134.7, 131.2, 126.8, 124.3, 120.8, 120.3, 118.6 (J=318.8 Hz), 112.7, 111.2, 74.3, 56.0, 55.2, 49.4, 43.3, 34.2, 29.6, 29.1.

R(−)-2-Methoxy-11-hydroxy-N-propargylnoraporphine (16): R(−)-2-methoxy-10-((trifluoromethyl)sulfonyl)oxy-11-hydroxy-N-propargylnoraporphine was reduced using Mg, NH$_4$Oac, Pd/C catalyst in MeOH as described in Example 4.

EXAMPLE 8

General Procedure for the Synthesis of R(−)-2-methoxy-N-alkyl-11-hydroxyaporphine esters The appropriate R(−)-2-methoxy-11-hydroxy-N-alkyl-noraporphine (0.5 mmol), the corresponding acid (0.6 mmol) and a catalytic amount of 4-dimethylaminopyridine (DMAP) are dissolved in anhydrous dichloromethane (20 mL) under nitrogen. To the stirred mixture a solution of N,N'-dicyclohexylcarbodiimide (130 mg, 0.6 mmol) in anhydrous dichloromethane (6 mL) is added at room temperature. After 4 hours stirring at room temperature the reaction mixture is filtered and evaporated to dryness. The crude product is purified by means of column chromatography (e.g., 5:2 (vols) hexane: ethyl acetate) to obtain pure product.

EXAMPLE 9

General Procedure for the Synthesis of R(−)-2-methoxy-N-alkyl-11-hydroxyaporphine carbamates Carbamates can be prepared by any one of a variety of methods known in the art. The most direct route is by reaction of R(−)-2-methoxy-N-alkyl-11-hydroxyaporphine alcohols with the appropriate carbamoyl chloride or isocyanate.

EXAMPLE 10

In Vitro Affinity Assays

Affinity of R(−)-2-methoxy-11-hydroxyaporphine, and derivatives thereof, for the dopamine D$_1$ and D$_2$ receptors can be determined by radioligand competition assays (see, for example, Faedda et al., *Biochem. Pharmacol.* 38:473 (1989) and Baldessarini et al., *Mol. Pharmacol.* 42:856 (1992)). Affinity data for compounds of the invention is provided in Table 1 (structures shown below).

TABLE 1

| | Affinity at rat receptors. | |
|---|---|---|
| Compound | D$_1$(nM)[1] | D$_2$(nM)[2] |
| (3) | 46 ± 2.8 | 235 ± 32 |
| (15) | 1,690 ± 130 | 44 ± 8.3 |
| (1a) | 1,010 ± 105 | 1.9 ± 0.5 |

TABLE 1-continued

| | Affinity at rat receptors. | |
|---|---|---|
| Compound | D$_1$(nM)[1] | D$_2$(nM)[2] |
| (1b) | 3,410 ± 300 | 0.9 ± 0.3 |
| (8) | 6,450 ± 130 | 1.3 ± 0.4 |

[1]D$_1$: [$^3$H]SCH23390
[2]D$_2$: [$^3$H]nemonapride

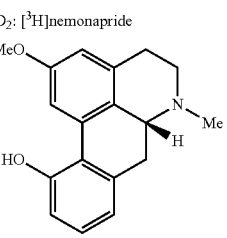

3

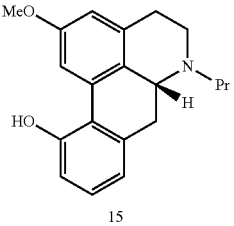

15

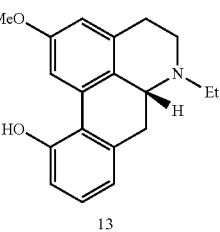

13

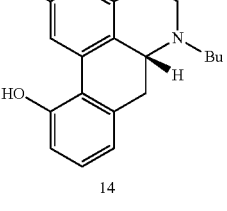

14

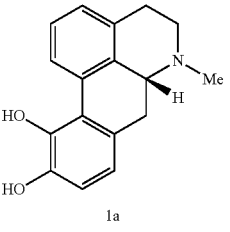 [SMILES: CN1CCc2cccc3c2[C@H]1Cc1ccc(O)c(O)c1-3]

1a

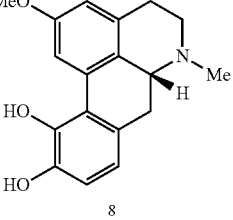

8

TABLE 1-continued

Affinity at rat receptors.

| Compound | $D_1(nM)^1$ | $D_2(nM)^2$ |
|---|---|---|

1b

1c

EXAMPLE 11

In Vivo Pharmacology

In vivo potency and oral bioavailability of the aporphine derivatives can be determined by measuring stimulation of motor activity in adult male Sprague-Dawley rats using a photobeam activity monitoring system (San Diego Instruments; San Diego, Calif.). See Zhang et al., *Neuropsychopharmacology* 25:624 (2001). Oral delivery of test agents is achieved using a permanently surgically pre-implanted polyethylene gastric tube to avoid stress associated with conventional oral intubation. For this surgery, rats are anesthetized with 60 mg/kg sodium pentobarbital intraperitoneally. PE50 tubing is inserted and sutured to the stomach, and led subcutaneously to a point of access on the back of the neck, where it is sutured in place. Animals are allowed two weeks to recover prior to behavior testing. The potency of the aporphine compounds is expressed as the sum of behavioral scores at each time of rating until locomotor responses returned to their pre-injection baseline levels, and relative to that (standard score=1) produced by intraperitoneal injection of 4 µmol/kg R(−)-apomorphine, the effects of which can last for one hour.

EXAMPLE 12

In Vitro Affinity at Human Receptors in Transfected Cell Membranes

Affinity data can be obtained in cells transfected with human $D_1$, $D_2$, or $D_3$ receptor cDNA. Cells are grown and harvested using standard procedures. Assays are performed using tritium-labeled ligands: SCH-23390 for $D_1$, nemonapride for $D_2$, and 7-OH-DPAT for $D_3$.

EXAMPLE 13

Rat Model of Hemiparkinsonism

Selective lesions of the nigrostrial DA pathway with the neurotoxin 6-hydroxydopamine (OHDA) results in slowly evolving denervation supersensitivity of postsynaptic DA receptors in neostriatum that is believed to mimic conditions found in clinical Parkinson's Disease. When adult rats with unilateral 6-OHDA lesions are challenged with drugs that interact with DA neurotransmission, rotational behavior occurs. Indirect DA agonists, such as methylphenidate and amphetamine, that block the neuronal reuptake, induce ipsilateral rotation toward the lesioned side, whereas direct receptor agonists, such as R(−)-apomorphine, induce rotation contralateral to the lesion (U. Ungerstadt, *Acta Physiol. Scand.* 82:51 (1971); and U. Ungerstadt, *Acta Physiol. Scand.* 82:69 (1971)).

These robust and quantifiable behavioral responses are believed to reflect laterally biased DA transmission caused by DA overflow in the intact side induced by indirect agonists and stimulation of supersensitized postsynaptic DA receptors in the lesioned side by direct agonists.

Unilateral 6-OHDA lesioning of the nigrostriatal DA pathway is carried out as detailed previously (see Creese et al., *Science* 197:596 (1977); and Zhang et al., *Pharmacol. Biochem. Behav.* 69:111 (2001)). Adult male Sprague-Dawley rats initially weighing 220 to 250 grams are maintained individually under a 12 hour artificial light/dark schedule (on, 07:00-19:00 h) with free access to standard rat chow and tap water. Rats are pretreated with the monoamine oxidase inhibitor pargyline hydrochloride (30 mg/kg, i.p., to potentiate the toxic amine) 60 minutes prior to microinfusion of 6-OHDA hydrobromide under anesthesia produced by sodium pentobarbital (60 mg/kg, i.p.). The neurotoxin (equivalent to 20 µg free base in 2 µl of 0.9% (w/v) saline containing 1 mM ascorbic acid) is injected to substantia nigra compacta over 2 minutes using a stereotaxic holder, with an additional 5 minutes allowed for equilibration of toxin in tissue. The stereotactic coordinates are: A–P=−5.8, D–V=8.0, L=2.0 mm, with the incisor bar set at 3.0 mm below zero. Rats are allowed 2 weeks to recover from the surgery before behavioral testing.

Rotational behavior is monitored visually in a clear Plexiglas hemispherical chamber (21 cm radius) by an experienced observer between 10:00 h and 16:00 h to minimize variance due to circadian rhythms. Subjects are initially screened for rotational behavior with an acute challenge with R(−)-apomorphine (0.5 mg/kg, i.p.). Rats displaying robust and consistent contralateral rotations are used further to test novel agents. The number of complete (360°) rotations is accumulated for 30 minutes after rotation begins. Rats are decapitated 72 hours after testing for histological verification of lesions, using autoradiographic analysis with [$^3$H]β-CIT, an improved radioligand to label the DA transporter (DAT) protein (see Kula et al., *Eur. J. Pharmacol.* 331:333 (1997); and Zhang et al., *Neuropsychopharmacology,* 25:624 (2001)).

Other Embodiments

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

What is claimed is:

1. A compound of formula I:

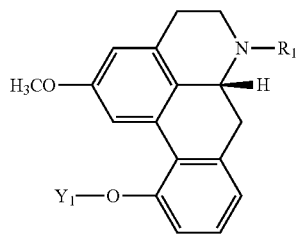
(I)

or a pharmaceutically acceptable salt thereof,
wherein
$Y_1$ is H, C(O)—$R_3$, C(O)—O—$R_3$, P(O)(OH)—O—$R_3$, C(S)—$R_3$, C(S)—O—$R_3$, C(S)—$NR_3R_4$, or fatty acid acyl;
$R_1$ is H, $C_{1-4}$ alkyl, $C_{2-4}$ alkenyl, or $C_{2-4}$ alkynyl; and
each of $R_3$ and $R_4$ is, independently, selected from H, $C_{1-12}$ alkyl, $C_{2-12}$ alkenyl, $C_{2-12}$ alkynyl, $C_{2-6}$ heterocyclyl, $C_{6-12}$ aryl, $C_{7-14}$ alkaryl, $C_{3-10}$ alkheterocyclyl, and $C_{1-7}$ heteroalkyl, or $R_3$ and $R_4$ together form a heterocyclic ring containing at least one nitrogen atom.

2. The compound of claim 1, wherein $R_1$ is H, $CH_3$, $CH_2CH_3$, $CH_2CH_2CH_3$, $CH_2CH_2$=$CH_2$, $CH_2C$≡$CH$, $CH_2CH_2CH_2CH_3$, or cyclopropylmethyl.

3. The compound of claim 1, wherein said compound is selected from R(−)-2-methoxy-11-hydroxy-N-n-propyl-noraporphine, R(−)-2-methoxy-11-hydroxy-N-methyl-noraporphine, R(−)-2-methoxy-11-hydroxy-N-ethyl-noraporphine, R(−)-2-methoxy-11-hydroxy-N-cyclopropylmethyl-noraporphine, R(−)-2-methoxy-11-hydroxy-N-propargyl-noraporphine, R(−)-2-methoxy-11-hydroxy-N-butyl-noraporphine, R(−)-2-methoxy-11-hydroxy-N-allyl-noraporphine, and pharmaceutically acceptable salts thereof.

4. The compound of claim 1, wherein said compound is selected from R(−)-2-methoxy-11-O-acetyl-N-n-propyl-noraporphine, R(−)-2-methoxy-11-O-propionyl-N-n-propyl-noraporphine, R(−)-2-methoxy-11-O-isobutyryl-N-n-propyl-noraporphine, R(−)-2-methoxy-11-O-butyryl-N-n-propyl-noraporphine, R(−)-2-methoxy-11-O-isovaleryl-N-n-propyl-noraporphine, R(−)-2-methoxy-11-O-valeryl-N-n-propyl-noraporphine, and pharmaceutically acceptable salts thereof.

5. A method of treating Parkinson's disease in a patient, said method comprising administering to said patient an effective amount of a compound of claim 1.

6. A method of treating sexual dysfunction in a patient, said method comprising administering to said patient an effective amount of a compound of claim 1.

7. The method of claim 5, wherein said compound is administered orally.

8. The method of claim 5, wherein said compound is administered intravenously.

9. The method of claim 5, wherein said compound is administered subcutaneously.

10. The method of claim 5, further comprising the administering to said patient of an effective amount of an anti-emetic agent simultaneously or within one day of administering said compound.

11. The method of claim 10 wherein said anti-emetic agent is nicotine, lobeline sulfate, pipamazine, oxypendyl hydrochloride, ondansetron, buclizine hydrochloride, cyclizine hydrochloride, dimenhydrinate, scopolamine, metopimazine, diphenhydramine, or diphenidol hydrochloride.

12. A method for synthesizing a compound of formula III from a compound of formula II:

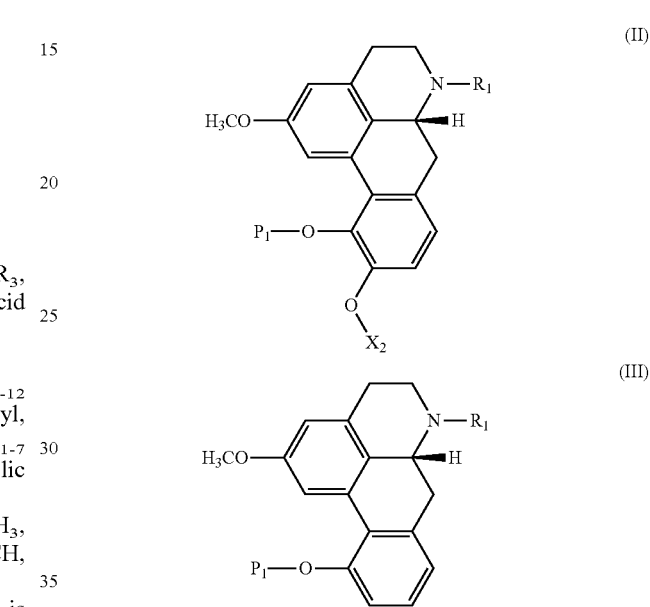

said method comprising the step of reducing said compound of formula II with magnesium metal in methanol in the presence of Pd/C catalyst, wherein
$P_1$ is H, or a hydroxyl protecting group other than $CH_3SO_2$— or $CF_3SO_2$—;
$X_2$ is $CH_3SO_2$— or $CF_3SO_2$—; and
$R_1$ is H, $C_{1-4}$ alkyl, $C_{2-4}$ alkenyl, $C_{2-4}$ alkynyl, or an amine protecting group.

13. The method of claim 12, wherein $P_1$ is H, C(O)—$R_3$, C(O)—O—$R_3$, C(O)—$NR_3R_4$, or $SiR_3R_4R_5$; and each of $R_3$, $R_4$, and $R_5$ is, independently, selected from H, $C_{1-12}$ alkyl, $C_{2-12}$ alkenyl, $C_{2-12}$ alkynyl, $C_{2-6}$ heterocyclyl, $C_{6-12}$ aryl, $C_{7-14}$ alkaryl, $C_{3-10}$ alkheterocyclyl, and $C_{1-7}$ heteroalkyl, or $R_3$ and $R_4$ together form a heterocyclic ring containing at least one nitrogen atom.

14. The method of claim 12, wherein said reducing is carried out in a solution comprising ammonium acetate.

15. The method of claim 12, wherein $R_1$ is $CH_3$, $CH_2CH_3$, $CH_2CH_2CH_3$, $CH_2CH_2$=$CH_2$, C≡CH, $CH_2CH_2CH_2CH_3$, or cyclopropylmethyl.

16. The compound of claim 3, wherein said compound is R(−)-2-methoxy-11-hydroxy-N-methyl-noraporphine or a pharmaceutically acceptable salt thereof.

17. The compound of claim 3, wherein said compound is R(−)-2-methoxy-11-hydroxy-N-n-propyl-noraporphine or a pharmaceutically acceptable salt thereof.

18. The compound of claim 3, wherein said compound is R(−)-2-methoxy-11-hydroxy-N-ethyl-noraporphine or a pharmaceutically acceptable salt thereof.

19. The compound of claim 3, wherein said compound is R(−)-2-methoxy-11-hydroxy-N-butyl-noraporphine or a pharmaceutically acceptable salt thereof.

* * * * *

UNITED STATES PATENT AND TRADEMARK OFFICE
CERTIFICATE OF CORRECTION

| | | |
|---|---|---|
| PATENT NO. | : 8,431,591 B2 | Page 1 of 1 |
| APPLICATION NO. | : 12/668617 | |
| DATED | : April 30, 2013 | |
| INVENTOR(S) | : John L. Neumeyer et al. | |

It is certified that error appears in the above-identified patent and that said Letters Patent is hereby corrected as shown below:

In the Claims

Column 30, Claim 15, Line 57, replace "C≡CH," with --$CH_2C{\equiv}CH$,--.

Signed and Sealed this
Seventh Day of January, 2014

Margaret A. Focarino
*Commissioner for Patents of the United States Patent and Trademark Office*

UNITED STATES PATENT AND TRADEMARK OFFICE
CERTIFICATE OF CORRECTION

| | | |
|---|---|---|
| PATENT NO. | : 8,431,591 B2 | Page 1 of 1 |
| APPLICATION NO. | : 12/668617 | |
| DATED | : April 30, 2013 | |
| INVENTOR(S) | : Neumeyer et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 557 days.

Signed and Sealed this
Third Day of March, 2015

Michelle K. Lee
*Deputy Director of the United States Patent and Trademark Office*